United States Patent
Fan et al.

(10) Patent No.: US 12,168,691 B2
(45) Date of Patent: Dec. 17, 2024

(54) VHS FORMAT BI-SPECIFIC ANTIBODIES SPECIFIC FOR HER2 AND VEGF AND USE THEREOF

(71) Applicant: Board of Regents, The University of Texas System, Austin, TX (US)

(72) Inventors: Zhen Fan, Houston, TX (US); Yang Lu, Houston, TX (US); Songho Qiu, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 216 days.

(21) Appl. No.: 17/058,414

(22) PCT Filed: May 31, 2019

(86) PCT No.: PCT/US2019/034836
§ 371 (c)(1),
(2) Date: Nov. 24, 2020

(87) PCT Pub. No.: WO2019/232323
PCT Pub. Date: Dec. 5, 2019

(65) Prior Publication Data
US 2021/0198370 A1    Jul. 1, 2021

Related U.S. Application Data

(60) Provisional application No. 62/678,733, filed on May 31, 2018.

(51) Int. Cl.
| | |
|---|---|
| A61K 39/395 | (2006.01) |
| A61K 45/06 | (2006.01) |
| A61P 35/04 | (2006.01) |
| C07K 16/22 | (2006.01) |
| C07K 16/28 | (2006.01) |
| A61K 39/00 | (2006.01) |

(52) U.S. Cl.
CPC ...... *C07K 16/2863* (2013.01); *A61K 39/3955* (2013.01); *A61K 45/06* (2013.01); *A61P 35/04* (2018.01); *C07K 16/22* (2013.01); *A61K 2039/505* (2013.01); *A61K 2039/545* (2013.01); *C07K 2317/31* (2013.01); *C07K 2317/622* (2013.01)

(58) Field of Classification Search
None
See application file for complete search history.

(56) References Cited

U.S. PATENT DOCUMENTS

| | | |
|---|---|---|
| 9,605,043 B2 | 3/2017 | Hong et al. |
| 2004/0063911 A1 | 4/2004 | Defrees et al. |
| 2004/0133357 A1 | 7/2004 | Zhong et al. |
| 2005/0142133 A1 | 6/2005 | Lazar et al. |
| 2006/0018899 A1 | 1/2006 | Kao et al. |
| 2006/0088523 A1 | 4/2006 | Andya et al. |
| 2009/0041770 A1 | 2/2009 | Chamberlain et al. |
| 2009/0148905 A1 | 6/2009 | Ashman et al. |
| 2015/0044216 A1 | 2/2015 | Wu et al. |
| 2015/0183867 A1 | 7/2015 | Ghayur et al. |
| 2016/0194399 A1 | 7/2016 | Irving et al. |
| 2017/0291955 A1 | 10/2017 | Li et al. |

FOREIGN PATENT DOCUMENTS

WO    WO 2017/182672    10/2017

OTHER PUBLICATIONS

Kontermann (2012) mAbs 4(2): 182-197. Dual targeting strategies with bispecific antibodies.*
Zhang et al. Int. J. Cancer 131(4): 956-969, 2012. A dual-targeting antibody against EGFR-VEGF for lung and head and neck cancer treatment.*
Brinkman et al. mAbs 9(2): 182-212, 2017. The making of bispecific antibodies.*
Jakob et al. (mAbs 5(3): 358-363, 2013).*
Singh et al. Exp. Mol. Med. 45: 1-11, 2013.*
Spiess et al. (Mol. Immunology 67: 95-106, 2015).*
Bostrom et al., "Variants of the antibody Herceptin that interact with HER2 and VEGF at the antigen binding site," *Science*, 323:1610-1614, 2009.
Byrne et al., "A tale of two specificities: bispecific antibodies for therapeutic and diagnostic applications," *Trends in Biotechnology*, 31(11):621-632, 2013.
Foy et al., "Combination treatment with HER-2 and VEGF peptide mimics induces potent anti-tumor and anti-angiogenic responses in vitro and in vivo," *J Biol Chem*, 286:13626-13637, 2011.
Gianni et al., "AVEREL: a randomized phase III Trial evaluating bevacizumab in combination with docetaxel and trastuzumab as first-line therapy for HER2-positive locally recurrent/metastatic breast cancer," *J Clin Oncol*, 31:1719-1725, 2013.
Kodack et al., "Combined targeting of HER2 and VEGFR2 for effective treatment of HER2-amplified breast cancer brain metastases," *Proc Natl Acad Sci U S A*, 109:E3119-E3127, 2012.

(Continued)

*Primary Examiner* — Christine J Saoud
(74) *Attorney, Agent, or Firm* — Parker Highlander PLLC

(57) ABSTRACT

The present disclosure provides a bispecific antibody comprising an IgG linked to an scFv, wherein the VH domain of the IgG is linked to the VH domain of the scFv, the bispecific antibody binding a human vascular endothelial growth factor (VEGF) family protein and an epidermal growth factor receptor (EGFR) family protein. Further embodiments provide pharmaceutical compositions comprising the bispecific antibody of the embodiments and aspects thereof and a pharmaceutically acceptable carrier. Further embodiments provide various methods of treating cancer in a subject comprising administering a bispecific antibody of the embodiments and aspects thereof to the subject. A further embodiment provides a kit comprising the bispecific antibody.

4 Claims, 19 Drawing Sheets

Specification includes a Sequence Listing.

(56) References Cited

OTHER PUBLICATIONS

Konecny et al., "Association between HER-2/neu and vascular endothelial growth factor expression predicts clinical outcome in primary breast cancer patients," *Clin Cancer Res*, 10:1706-1716, 2004.

Spiess et al., "Alternative molecular formats and therapeutic applications for bispecific antibodies," *Molecular Immunology*, 67:95-106, 2015.

\* cited by examiner

TB-VHS protein sequences

Heavy chain (VL-T → linker → VH-T → linker → VH-B → CH1 to CH3 human IgG1 constant domains)

DIQMTQSPSSLSASVGDRVTITCRASQDVNTAVAWYQQKPGKAPKLLIYSASFLYSGVPSRFSGSRSGTDFTLTISSLQPEDFATY
YCQQHYTTPPTFGQGTKVEIKGGGGSGGGGSGGGGSEVQLVESGGGLVQPGGSLRLSCAASGFNIKDTYIHWVRQAPGKGL
EWVARIYPTNGYTRYADSVKGRFTISADTSKNTAYLQMNSLRAEDTAVYYCSRWGGDGFYAMDYWGQGTLVTVSSASTKGP
EVQLVESGGGLVQPGGSLRLSCAASGYTFTNYGMNWVRQAPGKGLEWVGWINTYTGEPTYAADFKRRFTFSLDTSKSTAYL
QMNSLRAEDTAVYYCAKYPHYYGSSHWYFDVWGQGTLVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPGK

Light chain (VL-B → CL human IgG1 constant domain)

DIQMTQSPSSLSASVGDRVTITCSASQDISNYLNWYQQKPGKAPKVLIYFTSSLHSGVPSRFSGSGSGTDFTLTISSLQPEDF
ATYYCQQYSTVPWTFGQGTKVEIKRTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

FIG. 3A

BT-VHS protein sequences

Heavy chain (VL-B → linker → VH-B → linker → VH-T → CH1 to CH3 human IgG1 constant domains)

DIQMTQSPSSLSASVGDRVTITCSASQDISNYLNWYQQKPGKAPKVLIYFTSSLHSGVPSRFSGSGSGTDFTLTISSLQPEDFATY
YCQQYSTVPWTFGQGTKVEIKGGGGSGGGGSGGGGSEVQLVESGGGLVQPGGSLRLSCAASGYTFTNYGMNWVRQAPGK
GLEWVGWINTYTGEPTYAADFKRRFTFSLDTSKSTAYLQMNSLRAEDTAVYYCAKYPHYYGSSHWYFDVWGQGTLVTVSSAS
TKGPEVQLVESGGGLVQPGGSLRLSCAASGFNIKDTYIHWVRQAPGKGLEWVARIYPTNGYTRYADSVKGRFTISADTSKNTA
YLQMNSLRAEDTAVYYCSRWGGDGFYAMDYWGQGTLVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPGK

Light chain (VL-T → CL human IgG1 constant domain)

DIQMTQSPSSLSASVGDRVTITCRASQDVNTAVAWYQQKPGKAPKLLIYSASFLYSGVPSRFSGSRSGTDFTLTISSLQPEDFAT
YYCQQHYTTPPTFGQGTKVEIKRTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

FIG. 3B

XB-VHS protein sequences

Heavy chain (VL-X → linker → VH-X → linker → VH-B → CH1 to CH3 human IgG1 constant domains)

DILLTQSPVILSVSPGERVSFSCRASQSIGTNIHWYQQRTNGSPRLLIKYASESISGIPSRFSGSGSGTDFTLSINSVESEDIAD
YYCQQNNNWPTTFGAGTKLELK<u>GGGGSGGGGSGGGGS</u>QVQLKQSGPGLVQPSQSLSITCTVSGFSLTNYGVHWVRQS
PGKGLEWLGVIWSGGNTDYNTPFTSRLSINKDNSKSQVFFKMNSLQSNDTAIYYCARALTYYDYEFAYWGQGTLVTVSA
<u>ASTKG</u>PEVQLVESGGGLVQPGGSLRLSCAASGYTFTNYGMNWVRQAPGKGLEWVGWINTYTGEPTYAADFKRRFTFSL
DTSKSTAYLQMNSLRAEDTAVYYCAKYPHYYGSSHWYFDVWGQGTLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSCDKTHTCP
PCPAPELLGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHYTQKSLSLSPGK

Light chain (VL-B → CL human IgG1 constant domain)

DIQMTQSPSSLSASVGDRVTITCSASQDISNYLNWYQQKPGKAPKVLIYFTSSLHSGVPSRFSGSGSGTDFTLTISSLQPEDF
ATYYCQQYSTVPWTFGQGTKVEIKRTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

FIG. 3C

BX-VHS protein sequences

Heavy chain (VL-B → linker → VH-B→ linker → VH-X → CH1 to CH3 human IgG1 constant domains)

DIQMTQSPSSLSASVGDRVTITCSASQDISNYLNWYQQKPGKAPKVLIYFTSSLHSGVPSRFSGSGSGTDFTLTISSLQPEDFAT
YYCQQYSTVPWTFGQGTKVEIKGGGGSGGGGSGGGGSEVQLVESGGGLVQPGGSLRLSCAASGYTFTNYGMNWVRQAP
GKGLEWVGWINTYTGEPTYAADFKRRFTFSLDTSKSTAYLQMNSLRAEDTAVYYCAKYPHYYGSSHWYFDVWGQGTLVTVS
SASTKGPQVQLKQSGPGLVQPSQSLSITCTVSGFSLTNYGVHWVRQSPGKGLEWLGVIWSGGNTDYNTPFTSRLSINKDNSK
SQVFFKMNSLQSNDTAIYYCARALTYYDYEFAYWGQGTLVTVSAASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVVSVLTVLHQDWLNGKEYKCK
VSNKALPAPIEKTISKAKGQPREPQVYTLPPSREEMTKNQVSLTCLVKGFYPSDIAVEWESNGQPENNYKTTPPVLDSDGSFFL
YSKLTVDKSRWQQGNVFSCSVMHEALHNHYTQKSLSLSPGK

Light chain (VL-X → CL human IgG1 constant domain)

DILLTQSPVILSVSPGERVSFSCRASQSIGTNIHWYQQRTNGSPRLLIKYASESISGIPSRFSGSGSGTDFTLSINSVESEDIADY
YCQQNNNWPTTFGAGTKLELKRTVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC

VHS FORMAT BI-SPECIFIC ANTIBODIES SPECIFIC FOR HER2 AND VEGF AND USE THEREOF

This application is a national phase application under 35 U.S.C. § 371 of International Application No. PCT/US2019/034836, filed May 31, 2019, which claims the benefit of U.S. Provisional Patent Application No. 62/678,733 filed May 31, 2018, the entirety of each of which is incorporated herein by reference.

This invention was made with government support under grant numbers CA129036 and DE021883 awarded by the National Institutes of Health. The government has certain rights in the invention.

INCORPORATION OF SEQUENCE LISTING

The sequence listing that is contained in the file named "UTSC1334US_ST25.txt", which is 44,294 bytes (as measured in Microsoft Windows) and was created on Oct. 6, 2023, is filed herewith by electronic submission and is incorporated by reference herein.

BACKGROUND

1. Field

The present disclosure relates generally to the fields of molecular biology and medicine. More particularly, it concerns bispecific antibodies, such as for the treatment of cancer.

2. Description of Related Art

The anti-human epidermal growth factor receptor (EGFR) antibody cetuximab is effectively only in 10%-20% of patients with metastatic EGFR-overexpressing head and neck cancer and colorectal cancer. Similarly, the anti-human EGFR-2 (HER2) antibody trastuzumab is effective only in approximately 30%-50% of patients with HER2-overexpressing breast cancer. Cetuximab and trastuzumab cannot cure patients with metastatic disease. Therefore, better drugs are needed for the effective treatment of metastatic EGFR-overexpressing cancers and HER2-overexpressing cancers, such as breast cancer.

Vascular endothelial growth factor A (VEGFA), which is produced by both cancer cells and tumor stromal cells, promotes tumor development by stimulating tumor angiogenesis and by inducing an immunosuppressive tumor microenvironment. Preclinical studies indicated that VEGFA expression is regulated by EGFR and HER2 signaling in respective cancer types. VEGFA overexpression is correlated significantly with EGFR and HER2 overexpression-induced cancer aggressiveness in respective cancer types.

VEGFA downregulation by cetuximab or by trastuzumab is linked to clinical response to cetuximab or to trastuzumab in respective cancer types. The response of VEGFA downregulation is diminished after development of resistance to cetuximab or resistance to trastuzumab.

Bevacizumab, an anti-human VEGFA antibody, sequesters VEGFA through direct binding to VEGFA in the tumor microenvironment, including both cancer cell-derived VEGFA and stroma cell-derived VEGFA; however, clinical trials failed to show a survival benefit from combination of bevacizumab with cetuximab or trastuzumab in respective types of cancer patients.

Currently, there are no effective treatments for metastatic EGFR-overexpressing or HER2-overexpressing human cancers. Thus, there is an unmet need for new treatments for patients with EGFR-overexpressing or HER2-overexpressing metastatic cancer.

SUMMARY

In a first embodiment, the present disclosure provides a bispecific antibody comprising an IgG linked to an scFv, wherein the VH domain of the IgG is linked to the VH domain of the scFv, the bispecific antibody binding a human vascular endothelial growth factor (VEGF) family protein and an epidermal growth factor receptor (EGFR) family protein. In some aspects, the protein of the VEGF family is VEGF-A, VEGF-B, VEGF-C, or VEGF-D. In certain aspects, the protein of the EGFR family is EGFR or human epidermal growth factor receptor 2 (HER2).

In some aspects, the IgG comprises anti-VEGF VH and VL domains and the scFv comprises anti-EGFR VH and VL domains. In certain aspects, the IgG comprises anti-VEGF VH and VL domains and the scFv comprises anti-HER2 VH and VL domains. In some aspects, the IgG comprises anti-EGFR VH and VL domains and the scFv comprises anti-VEGF VH and VL domains. In certain aspects, the IgG comprises anti-HER2 VH and VL domains and the scFv comprises anti-VEGF VH and VL domains.

In some aspects, the antibody comprises an anti-VEGFA VH domain having at least 70%, 80%, 90%, 91%, 92%, 93%, 94%, 95%, 96%, 97%, 98%, or 99% identity to SEQ ID NO:9. In some aspects, the antibody comprises an anti-VEGFA VH domain of SEQ ID NO:9. In certain aspects, antibody comprises an anti-VEGFA VL domain having at least 70%, 80%, 90%, 91%, 92%, 93%, 94%, 95%, 96%, 97%, 98%, or 99% identity to SEQ ID NO:10. In some aspects, the antibody comprises an anti-VEGFA VL domain of SEQ ID NO:10.

In certain aspects, the antibody comprises an anti-HER2 VH domain having at least 70%, 80%, 90%, 91%, 92%, 93%, 94%, 95%, 96%, 97%, 98%, or 99% identity to SEQ ID NO:11. In some aspects, the antibody comprises an anti-HER2 VH domain of SEQ ID NO:11. In certain aspects, the antibody comprises an anti-HER2 VL domain having at least 70%, 80%, 90%, 91%, 92%, 93%, 94%, 95%, 96%, 97%, 98%, or 99% identity to SEQ ID NO:12. In particular aspects, the antibody comprises an anti-HER2 VL domain of SEQ ID NO:12.

In some aspects, the antibody comprises an anti-EGFR VH domain having at least 70%, 80%, 90%, 91%, 92%, 93%, 94%, 95%, 96%, 97%, 98%, or 99% identity to SEQ ID NO:13. In certain aspects, the antibody comprises an anti-EGFR VH domain of SEQ ID NO:13. In some aspects, the antibody comprises an anti-EGFR VL domain having at least 70%, 80%, 90%, 91%, 92%, 93%, 94%, 95%, 96%, 97%, 98%, or 99% identity to SEQ ID NO:14. In certain aspects, the antibody comprises an anti-EGFR VL domain of SEQ ID NO:14.

In certain aspects, the antibody comprises a heavy chain having at least 70%, 80%, 90%, 91%, 92%, 93%, 94%, 95%, 96%, 97%, 98%, or 99% identity to SEQ ID NO: 1, 3, 5, or 7. In particular aspects, the antibody comprises a heavy chain of SEQ ID NO: 1, 3, 5, or 7. In some aspects, the antibody comprises a light chain having at least 70%, 80%, 90%, 91%, 92%, 93%, 94%, 95%, 96%, 97%, 98%, or 99% identity to SEQ ID NO: 2, 4, 6, or 8. In certain aspects, the antibody comprises a light chain of SEQ ID NO: 2, 4, 6, or 8.

In specific aspects, the antibody comprises a heavy chain having at least 70%, 80%, 90%, 91%, 92%, 93%, 94%, 95%, 96%, 97%, 98%, or 99% identity to SEQ ID NO: 1 and a light chain having at least 95% identity to SEQ ID NO: 2. In particular aspects, the antibody comprises a heavy chain having of SEQ ID NO: 1 and a light chain of SEQ ID NO: 2.

In some aspects, the antibody comprises a heavy chain having at least 70%, 80%, 90%, 91%, 92%, 93%, 94%, 95%, 96%, 97%, 98%, or 99% identity to SEQ ID NO: 3 and a light chain having at least 95% identity to SEQ ID NO: 4. In specific aspects, the antibody comprises a heavy chain of SEQ ID NO: 3 and a light chain of SEQ ID NO: 4.

In certain aspects, the antibody comprises a heavy chain having at least 70%, 80%, 90%, 91%, 92%, 93%, 94%, 95%, 96%, 97%, 98%, or 99% identity to SEQ ID NO: 5 and a light chain having at least 95% identity to SEQ ID NO: 6. In some aspects, the antibody comprises a heavy chain of SEQ ID NO: 5 and a light chain of SEQ ID NO: 6.

In some aspects, the antibody comprises a heavy chain having at least 70%, 80%, 90%, 91%, 92%, 93%, 94%, 95%, 96%, 97%, 98%, or 99% identity to SEQ ID NO: 7 and a light chain having at least 95% identity to SEQ ID NO: 8. In specific aspects, the antibody comprises a heavy chain of SEQ ID NO: 7 and a light chain of SEQ ID NO: 8.

In some aspects, the IgG is further defined as IgG1. In certain aspects, the IgG comprises constant domains of SEQ ID NOs: 15 and 16. In some aspects, the VH and VL of the scFv are attached by a GGGGSGGGGSGGGGS (SEQ ID NO:17) linker. In certain aspects, the VH of the scFv is attached to the VH of the IgG by an ASTKGP (SEQ ID NO: 18) linker.

Further embodiments provide pharmaceutical compositions comprising the bispecific antibody of the embodiments and aspects thereof and a pharmaceutically acceptable carrier.

In another embodiment, there is provided a bispecific antibody of the embodiments and aspects thereof obtained by a method comprising the steps of transforming a host cell with vectors comprising nucleic acid molecules encoding said antibody; culturing the host cell under conditions that allow synthesis of said antibody molecule; and recovering said antibody molecule from said culture.

A further embodiment provides a method of treating cancer in a subject comprising administering a bispecific antibody of the embodiments and aspects thereof to the subject. In some aspects, the subject is a human.

In some aspects, the cancer is an EGFR-overexpressing cancer. In certain aspects, the cancer is a HER2-overexpressing cancer. In particular aspects, the cancer is breast cancer. In specific aspects, the breast cancer is metastatic breast cancer.

In certain aspects, the administering is daily, weekly, monthly, every other month, every three months, every four months, every five months, every six months, every nine months or every year.

In additional aspects, the method further comprises administering to said subject at least a second anti-cancer therapy. In some aspects, the anti-cancer therapy is chemotherapy, radiotherapy, gene therapy, surgery, hormonal therapy, anti-angiogenic therapy or immunotherapy.

In another embodiment, there is provided a hybridoma or engineered cell encoding a bispecific antibody of the embodiments and aspects thereof. A further embodiment provides a kit comprising a bispecific antibody of the embodiments and aspects thereof.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A-3D: Sequences of VHS bi-specific antibodies including (FIG. 3A) TB-VHS antibody (Heavy chain=SEQ ID NO: 3; Light Chain=SEQ ID NO: 4), (FIG. 3B) BT-VHS antibody (Heavy chain=SEQ ID NO: 1; Light Chain=SEQ ID NO: 2), (FIG. 3C) XB-VHS antibody (Heavy chain=SEQ ID NO: 5; Light Chain=SEQ ID NO: 6), and (FIG. 3D) BX-VHS antibody (Heavy chain=SEQ ID NO: 7; Light Chain=SEQ ID NO: 8).

XB-VHS and BX-VHS (100 nM) were respectively premixed with 3-fold were the incubated with EGFR-overexpressing MDA-MB-468 breast cancer cells. Left, Medium fluorescence intensity (MFI); right; Flow cytometry diagrams.

Figures 10A, 10B:
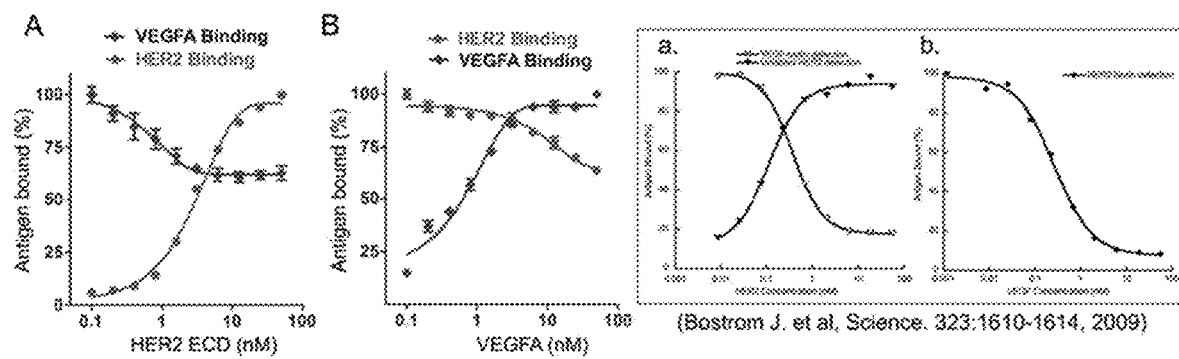

FIGS. 10A-10B: TB-VHS binds simultaneously to VEGFA and HER2 with only limited intramolecular steric hindrance. (FIG. 10A) TB-VHS was incubated with biotinylated VEGFA and increasing concentrations of HER2 extracellular domain (ECD) recombinant protein. (FIG. 10B) TB-VHS was incubated with HER2 ECD recombinant protein and increasing concentrations of biotinylated VEGFA and unlabeled VEGFA. Inset: Binding of a HER2-VEGFA 2-in-1 antibody (Bostrom et al., Science, 323:1610-1614, 2009).

Figures 11A, 11B, 11C:
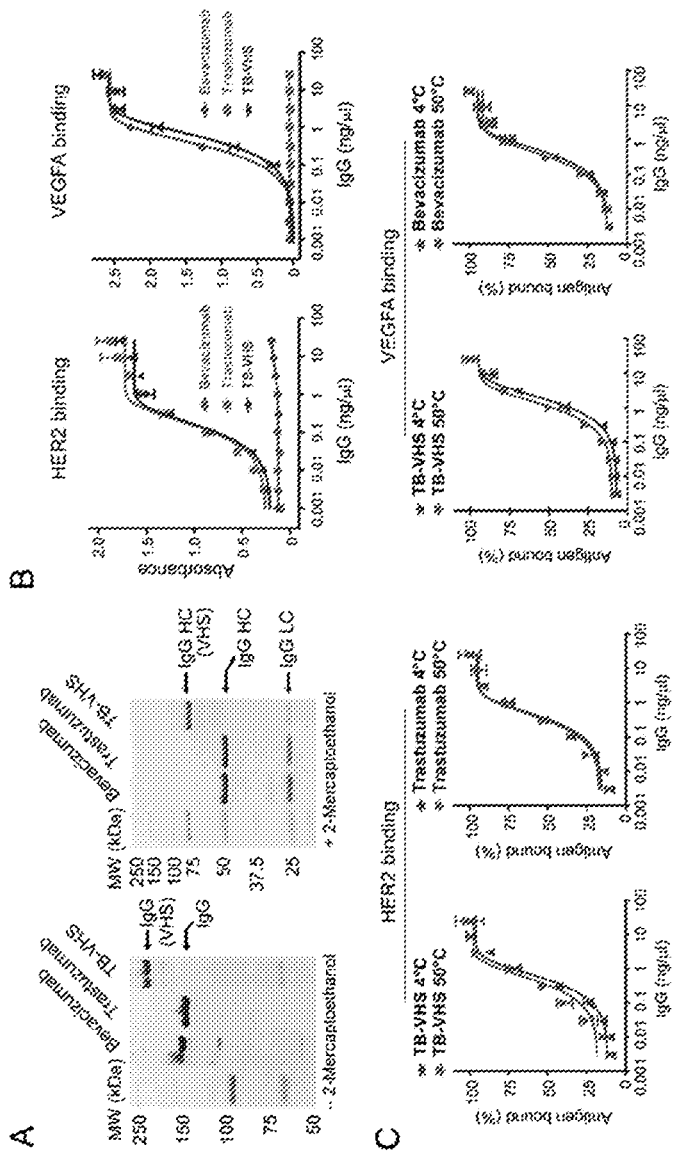

FIGS. 11A-11C: (FIG. 11A) Physiochemical properties and functional characterization of TB-VHS. (FIG. 11B) Specific binding of TB-VHS and its parent antibodies to human HER2 and human VEGFA by ELISA. (FIG. 11C) TB-VHS, bevacizumab, and trastuzumab were incubated in a water bath at 50° C. for 1 hour, and then these antibodies and antibodies stored at 4° C. were subjected as in FIG. 11B.

Figures 12A, 12B, 12C, 12D:
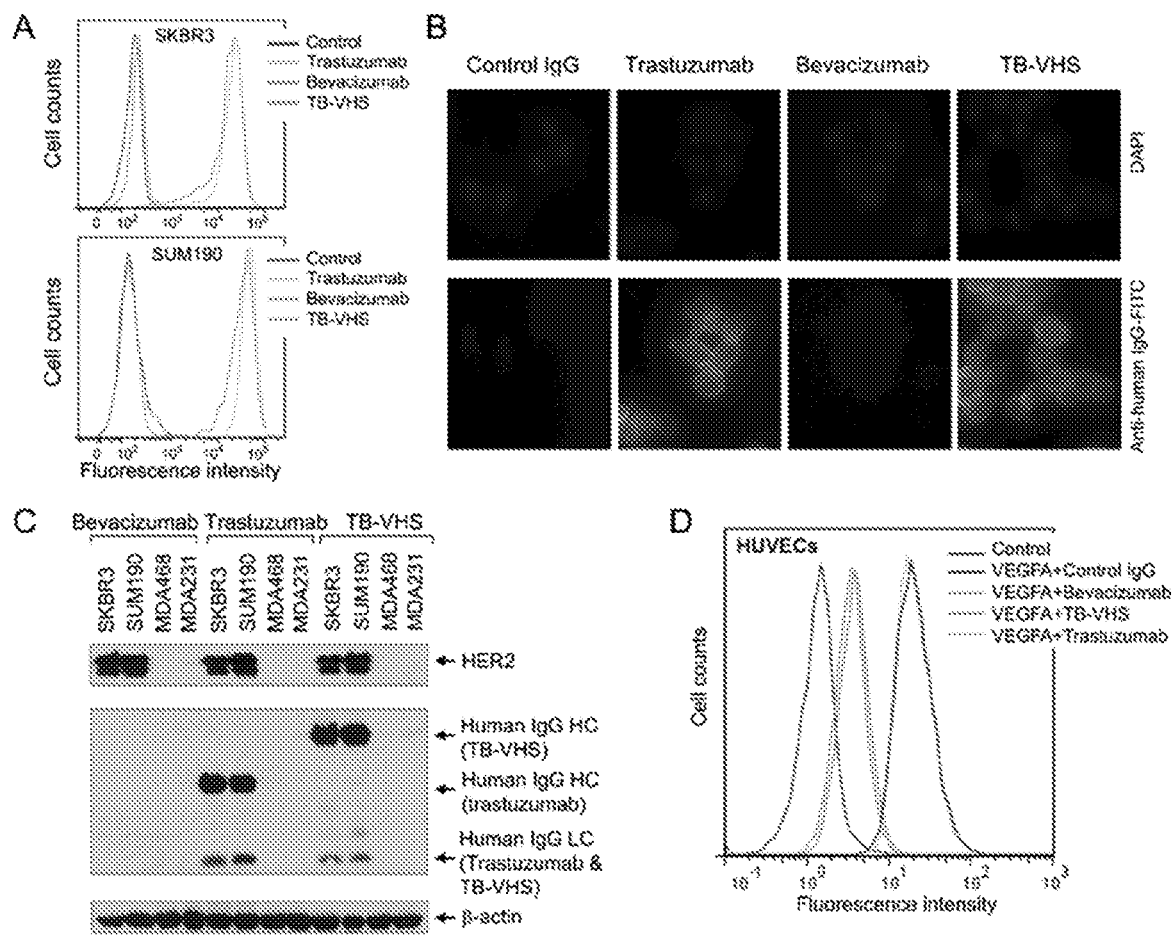

FIGS. 12A-12D: TB-VHS binds to HER2-overexpressing breast cancer cells and inhibits VEGFA binding to HUVECs. (FIGS. 12A, B) SKBR3, and SUM190 cells were incubated with control IgG, trastuzumab, bevacizumab, or TB-VHS and then stained with FITC-labelled anti-human IgG antibody for flow cytometry analysis (FIG. 12A) and observation under fluorescent microscope (only SUM190 cells are shown) (FIG. 12B). (FIG. 12C) The indicated breast cancer cell lines were incubated with 20 nM bevacizumab, trastuzumab, or TB-VHS on ice for 30 minutes. The cell lysates were then harvested and subjected to Western blotting with the antibodies shown at right. (FIG. 12D) Biotinylated VEGFA was incubated with the indicated antibodies on ice for 1 hour. The biotinylated VEGFA mixed with or without the antibodies was then incubated with HUVECs on ice for 1 hour. Cells were then washed, incubated for 30 minutes with FITC-labelled streptavidin (R&D Systems), and then subjected to flow cytometry analysis.

Figures 13A, 13B:
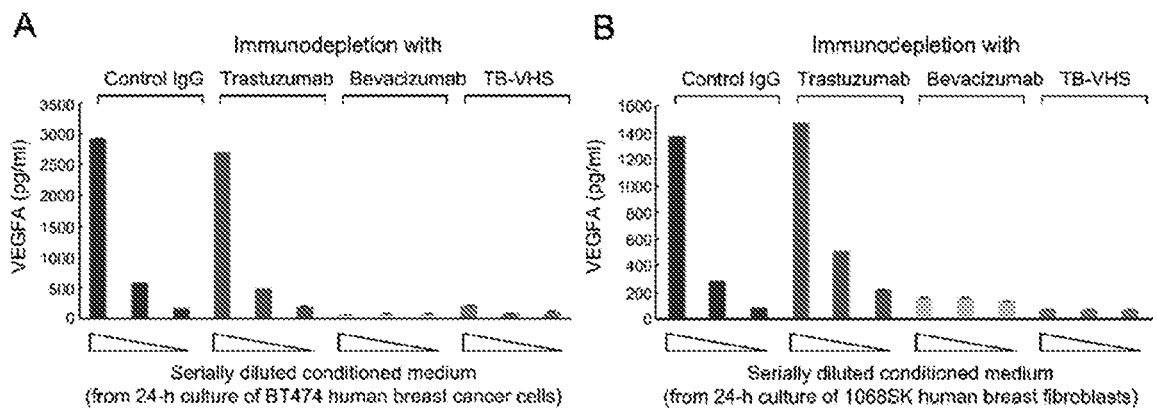

FIGS. 13A-13B: TB-VHS depletes VEGFA in conditioned medium from cultures of breast cancer cells and breast fibroblasts. VEGFA quantification in serially diluted conditioned medium from cultures of BT474 human breast cancer cells (FIG. 13A) and 1068K human breast fibroblasts (FIG. 13B) is shown.

Figures 14A, 14B, 14C:
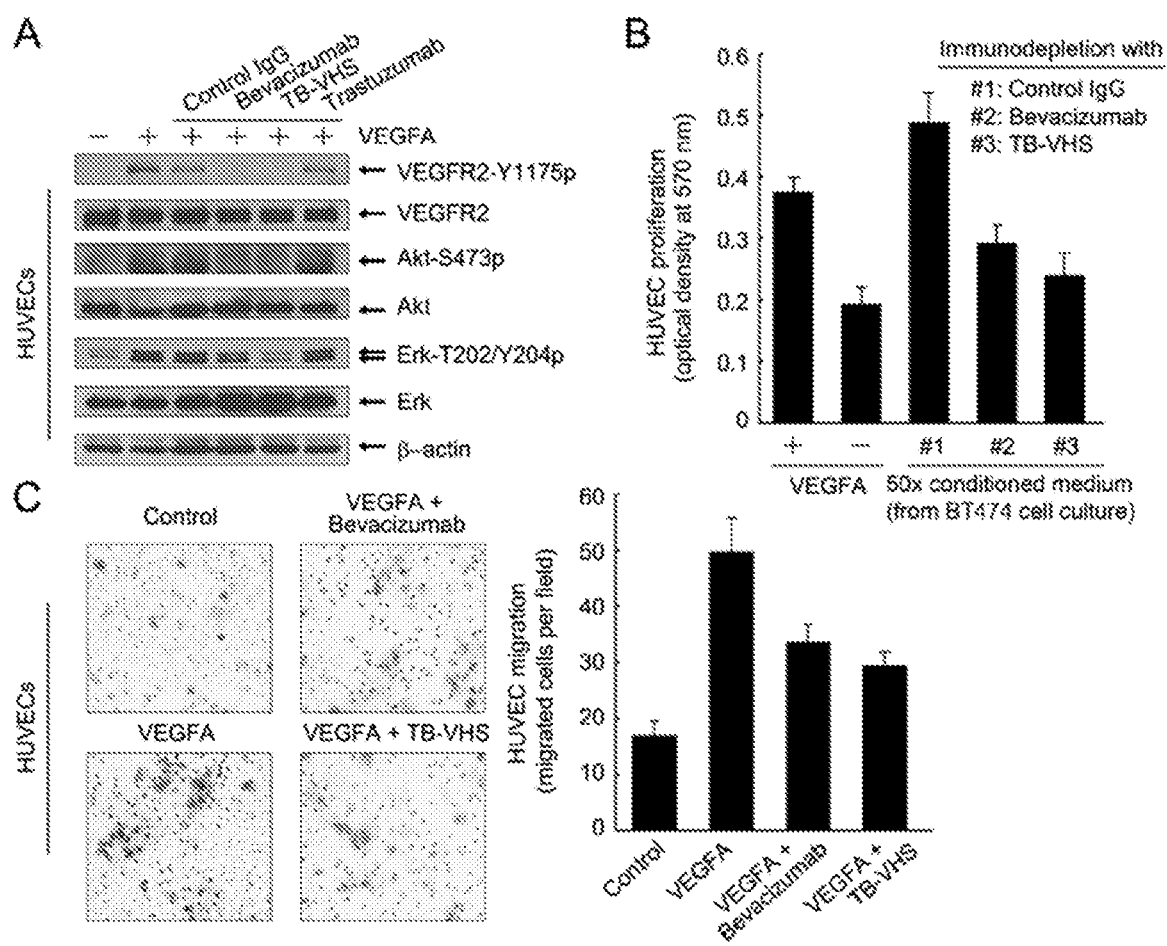

FIGS. 14A-14C: TB-VHS inhibits VEGFA-induced activation of cell signaling and VEGFA-induced proliferation and migration in HUVECs, acting similarly to bevacizumab. (FIG. 14A) HUVECs were untreated, treated with 150 ng/mL VEGFA for 2 minutes, or treated with 150 ng/mL VEGFA that was preincubated with control IgG, bevacizumab, TB-VHS, or trastuzumab. Cell lysates were analyzed by Western blotting with the antibodies shown at right. (FIG. 14B) HUVECs were cultured for 4 days in culture medium with or without VEGFA or in VEGFA-deficient medium supplemented with 50× concentrated conditioned medium from BT474 cell culture that was subjected to immunodepletion with the indicated antibodies by using procedures described in FIG. 9A. Cell proliferation was measured with AlamarBlue assay at 570 nm. (FIG. 14C) HUVECs ($5 \times 10^4$ cells) were seeded into the upper chamber of a Boyden chamber in 0.25 mL of medium with 0.75 mL of culture medium without (control) or with VEGFA, or the VEGFA in the medium was subjected to immunodepletion. Migration of HUVECS through the transwell membrane in the chamber was measured after 24 hours.

Figures 15A, 15B, 15C, 15D, 15E, 15F:
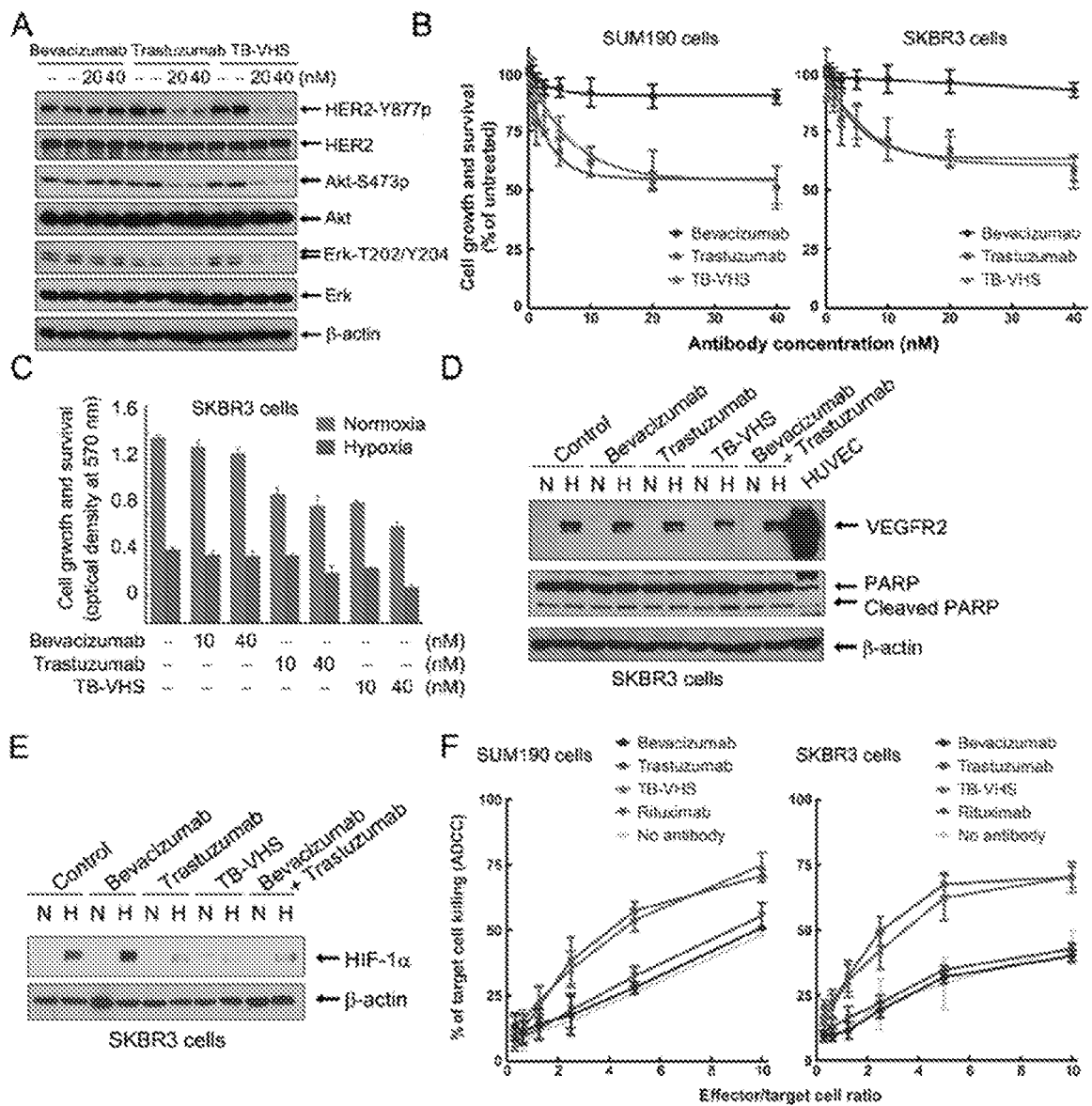

FIGS. 15A-15F: TB-VHS inhibits HER2-induced cell signaling and cell proliferation and induces ADCC in HER2-overexpressing breast cancer cells, acting similarly to trastuzumab. (FIG. 15A) SKBR3 breast cancer cells were untreated or treated with bevacizumab, trastuzumab, or TB-VHS for 24 hours. Cell lysates were analyzed by Western blotting with the antibodies shown at right. (FIGS. 15B, C) SUM190 and SKBR3 cells were treated with antibodies as indicated for 4 days (FIG. 15B) and SKBR3 cells were treated with antibodies as indicated for 4 days in normoxia or in a hypoxia chamber (FIG. 15C). Cell growth and survival were measured with MTT assay at 570 nm. (FIGS. 15D, E) SKBR3 cells were untreated or treated with antibodies shown at top for 24 hours under normoxia (N) or hypoxia (H). Cell lysates were analyzed by Western blotting with the antibodies shown at right. (FIG. 15F) SUM190 and SKBR3 cells were labeled with Calcein and then mixed with NK cells from healthy donors at the indicated effector/target ratios. The data shown are averages of 3 independent experiments.

Figures 16A, 16B:
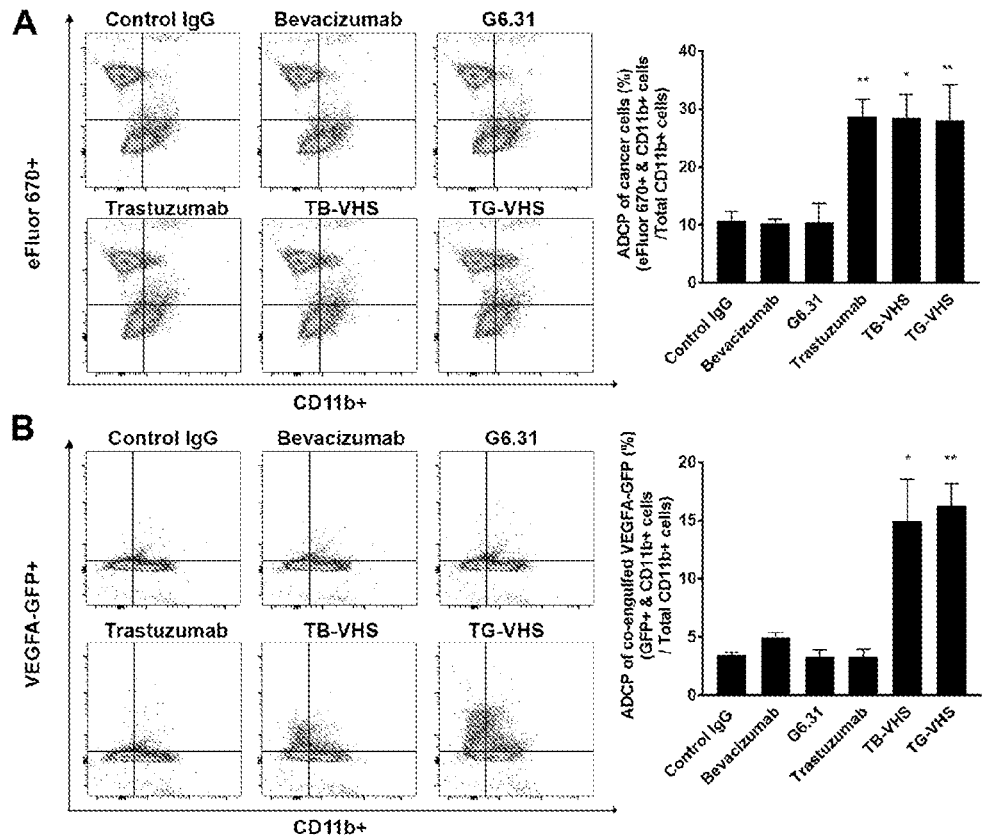

FIGS. 16A-16B: Breast cancer cells labeled with eFluor 670 cell proliferation marker were phagocytized by RAW264.7 macrophages when cells were co-cultured in the presence of trastuzumab, TB-VHS, or TG-VHS but not in the presence of bevacizumab, G6.31, or control antibody (FIG. 16A). Addition of VEGFA-GFP fusion protein in the co-culture resulted in co-engulfment of VEGFA-GFP into the RAW264.7 macrophages engaged by TB-VHS or TG-VHS but not the RAW264.7 macrophages engaged by trastuzumab, as detected by multicolor FACS (FIG. 16B).

Figures 17A, 17B:
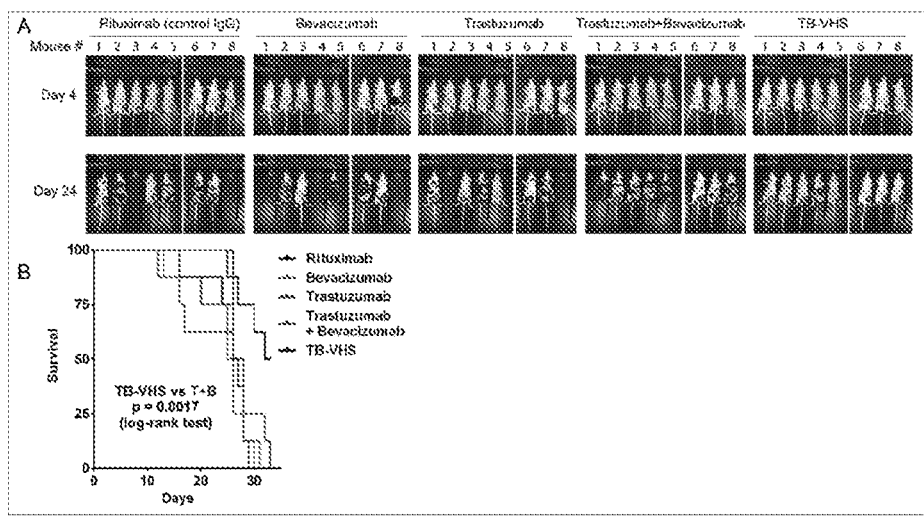

FIGS. 17A-17B: TB-VHS prolongs survival of nude mice transplanted with 4T1/HER2 tumors. (FIG. 17A) 4T1/HER2 mouse mammary tumor cells ($1 \times 10^6$ cells/mouse) were transplanted along with 3T3 fibroblasts transduced to express human VEGFA. (FIG. 17B) Survival curves of mice.

Figures 18A, 18B:
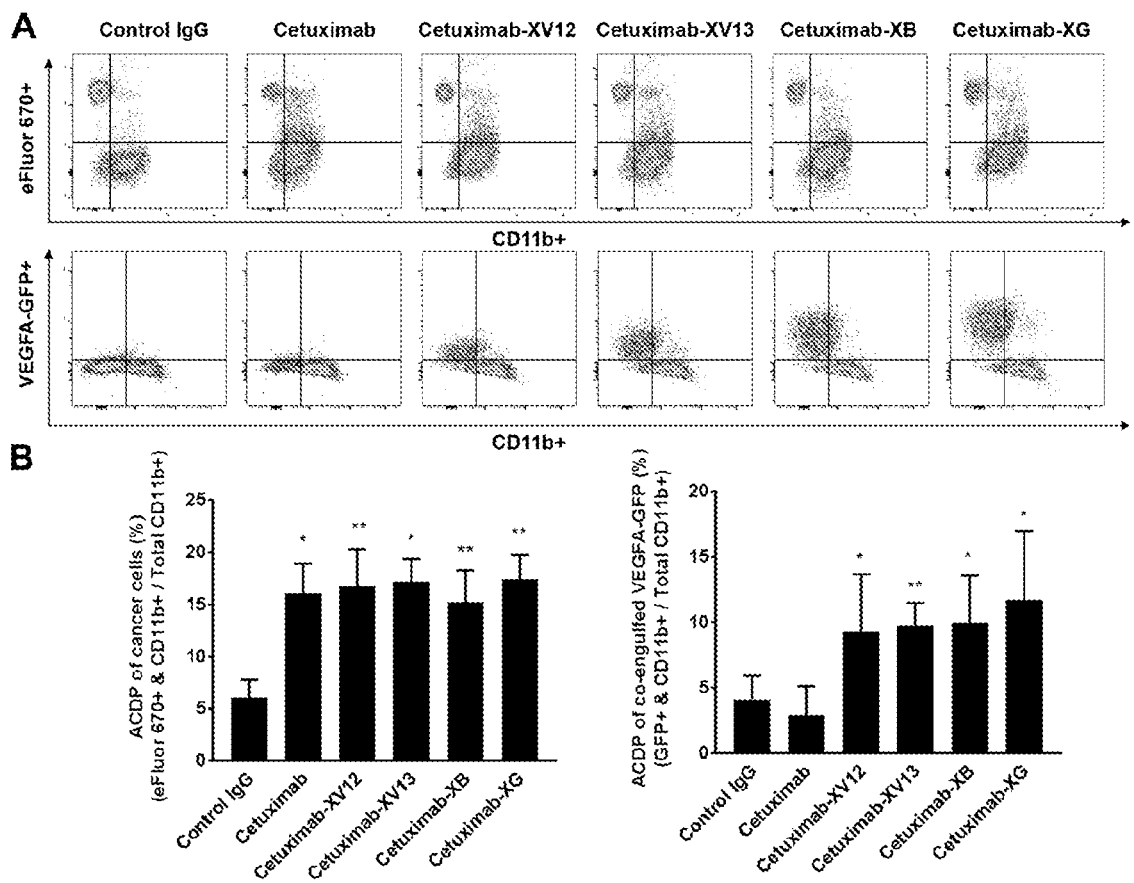

FIGS. 18A-18B: ADCP-mediated co-engulfment of VEGFA along with targeted cancer cells by cetuximab-XV12, cetuximab-XV13, cetuximab-XB, and cetuximab-XG, but not cetuximab. MDA-MB-468 cells were labeled with eFlour670 proliferation marker and co-incubated with RAW264.7 macrophages for 1 hr and a fusion protein human VEGF-GFP was added along with various agents during the incubation period. After the incubation, the cells were washed to remove any unbound antibodies and stained with anti-CD11b antibody for flow cytometry analysis. (FIG. 18A) Contour plots of flow cytometry data. (FIG. 18B) Quantitative analysis of cell counts of eFlour 670 and CD11b double-positive cells (left) or GFP (right) as a percentage of total CD11b positive cells. The bar graph data represent the average 3 experiments. *, $p<0.05$, **, $p<0.01$

DESCRIPTION OF ILLUSTRATIVE EMBODIMENTS

Figure 1:
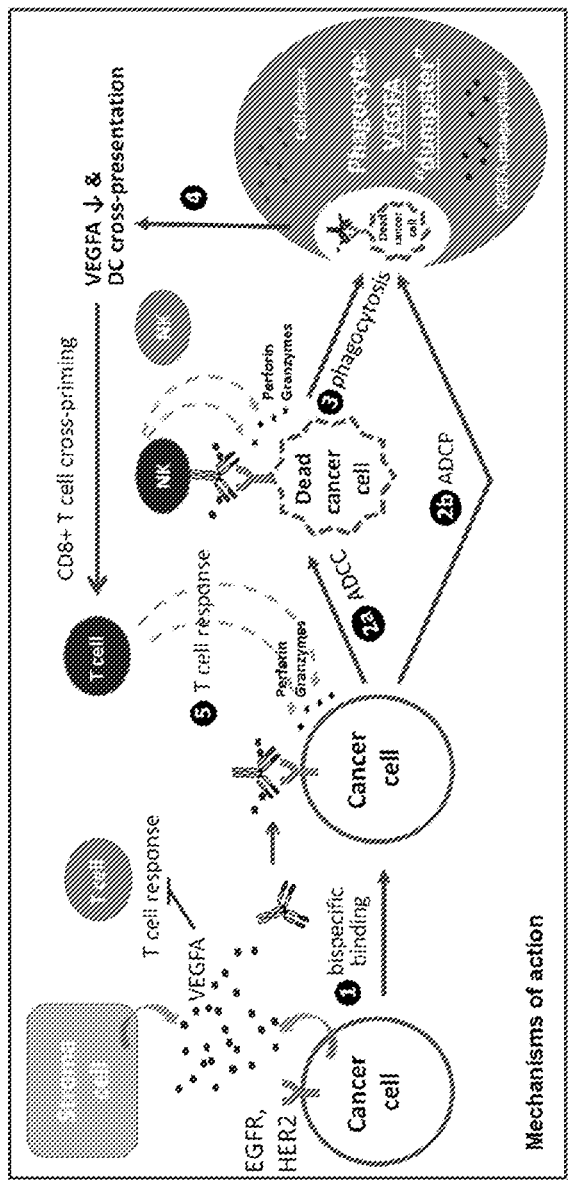
FIG. 1: Mechanisms of action of HER2-VEGFA or EGFR-VEGFA bispecific antibodies.
Figure 2A:
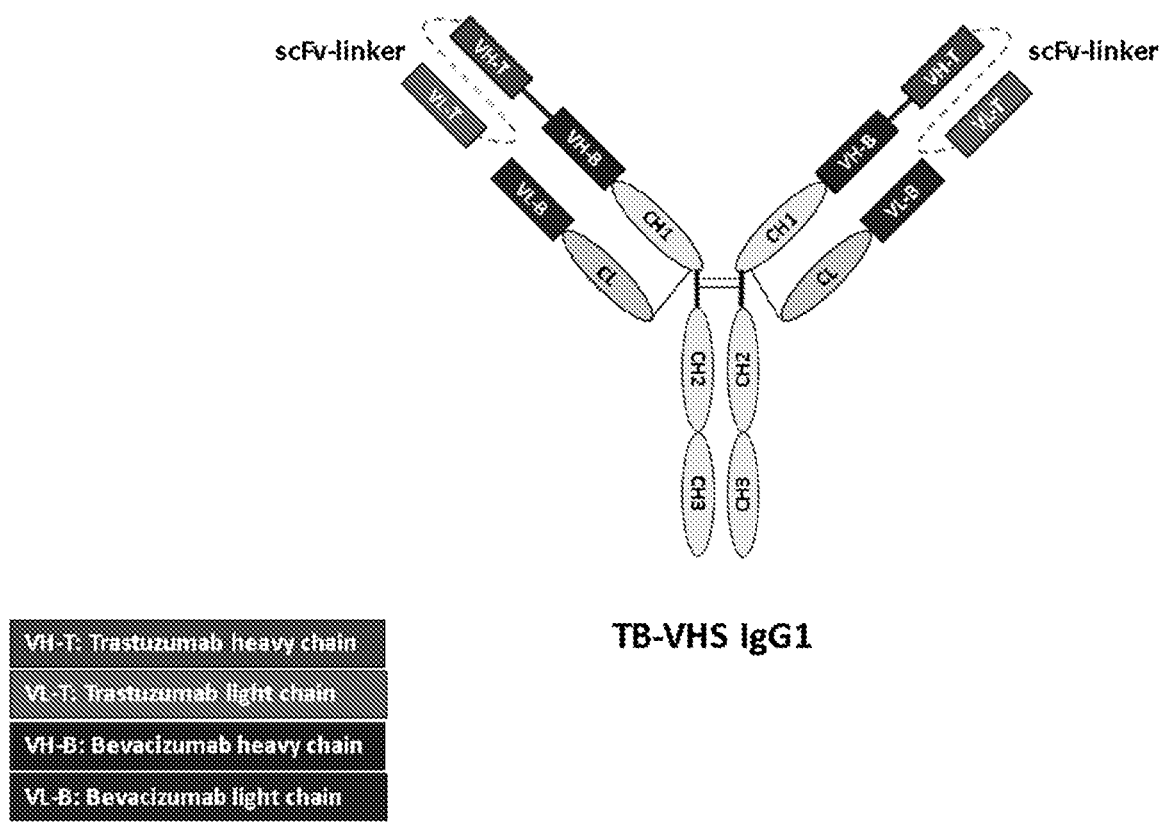
FIGS. 2A-2D: Schematic of VHS bi-specific antibody configurations for (FIGS. 2A, 2B) HER2 (trastuzumab) and VEGF (bevacizumab) or (FIGS. 2C, 2D) EGFR (cetuximab) and VEGF (bevacizumab).
Figure 2B:
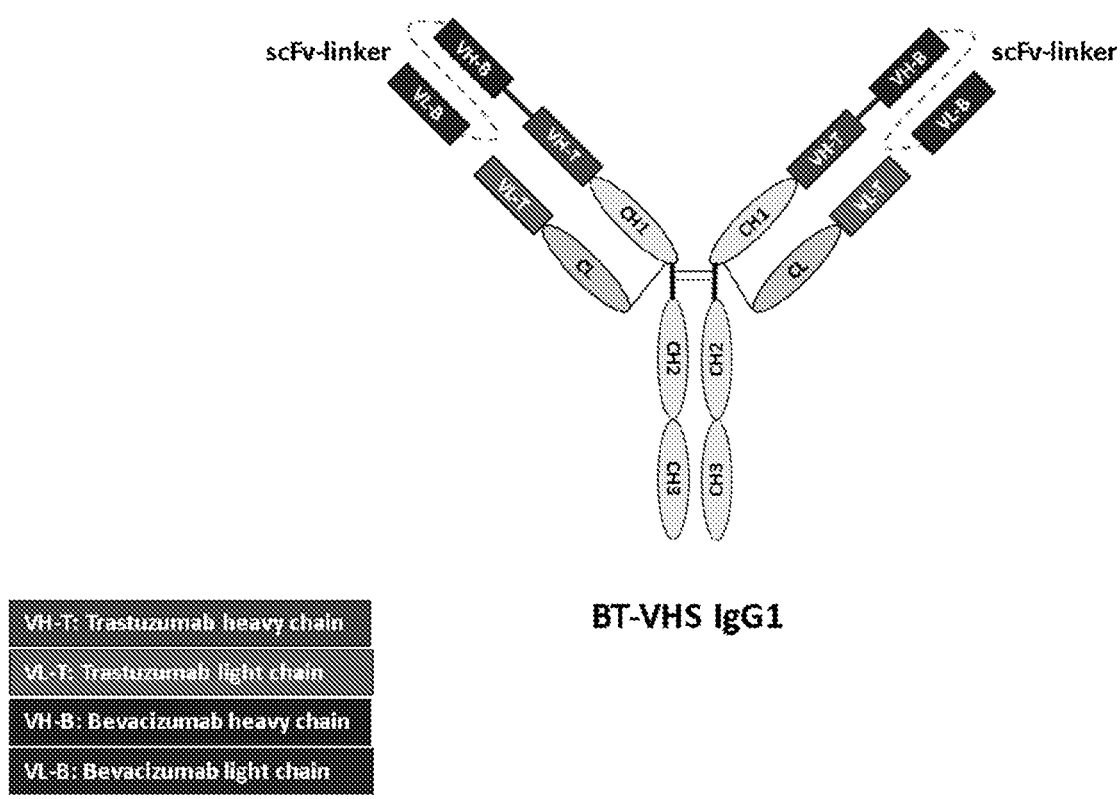
Figure 2C:
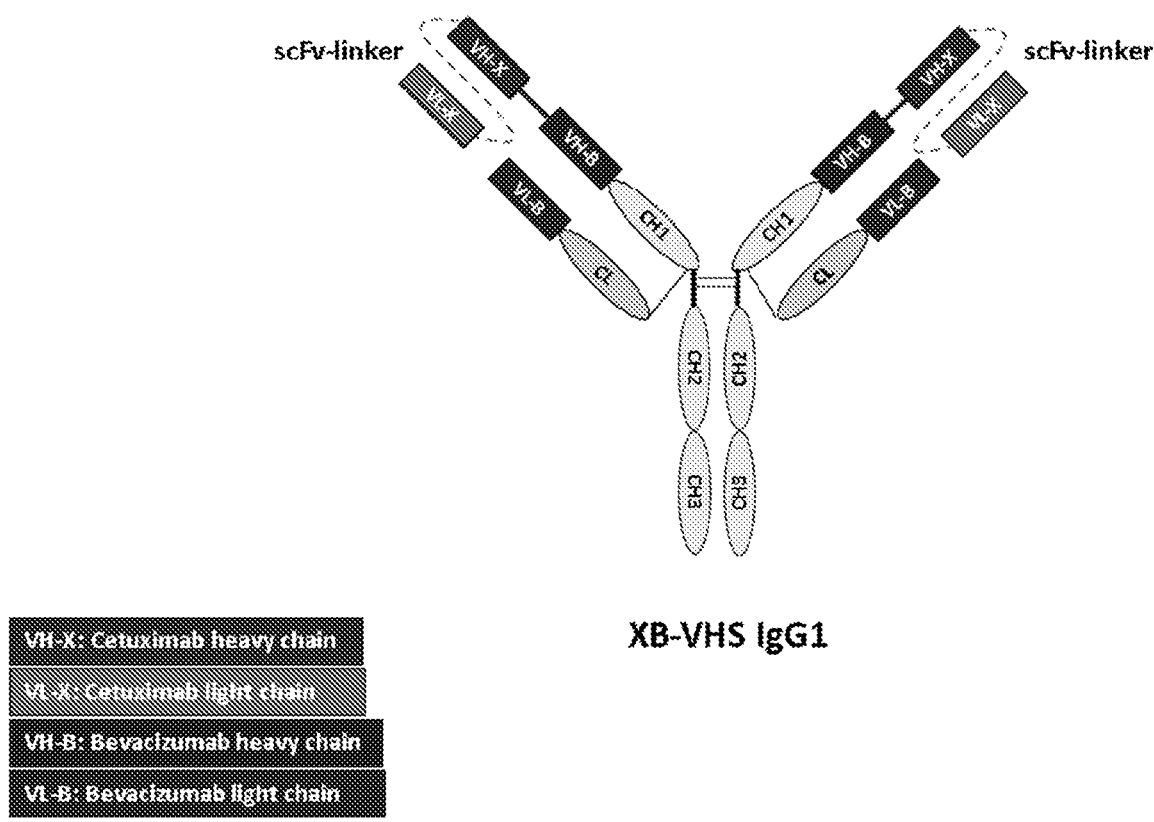
Figure 2D:
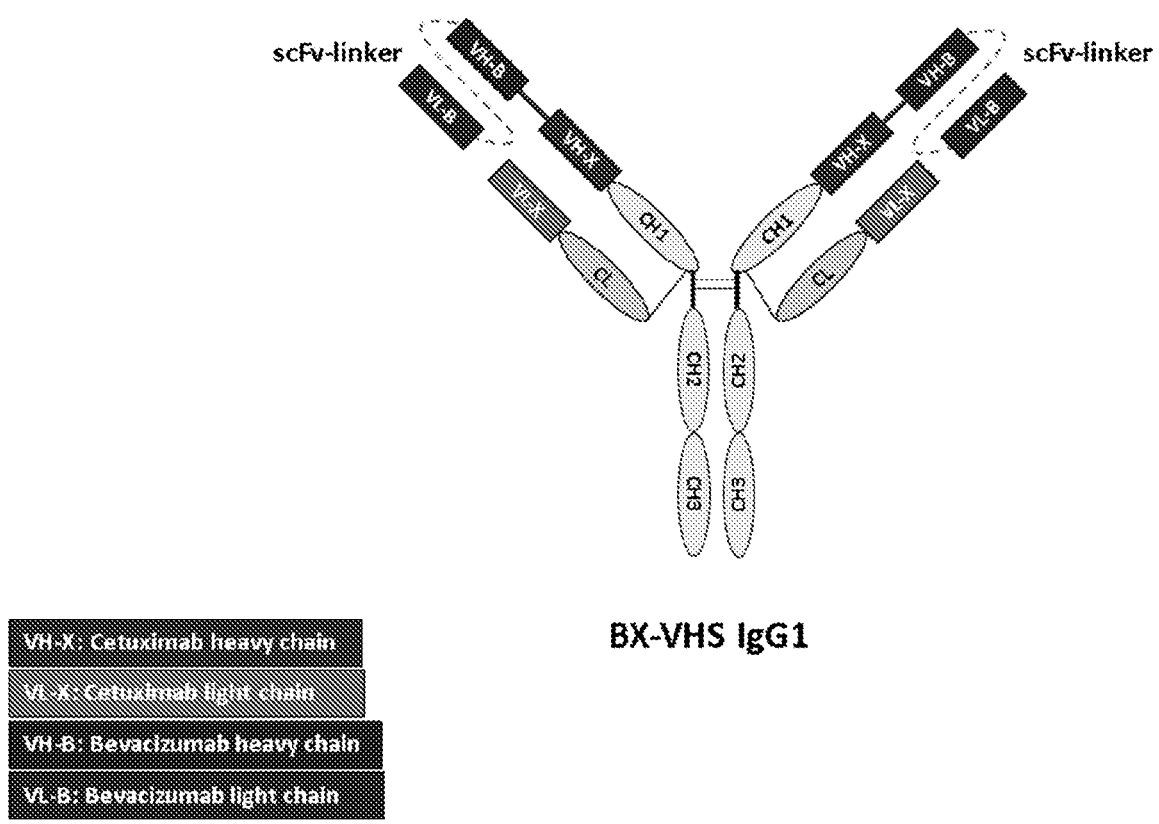

In certain embodiments, the present disclosure provides methods and compositions that permit delivery of anti VEGF and anti-EGFR, such as anti-VEGFA and anti-HER2 or anti-VEGFA and anti-EGFR, activities. The present bispecific antibodies (e.g., illustrated in FIG. 2) may generate strong antitumor activities via a novel mechanism of action that the parental antibodies cannot either alone or in combination. The bispecific antibody may target members of the EGFR family, such as but not limited to EGFR and HER2. The antibody may also target members of the VEGF family that are enriched in the tumor microenvironment and that are known to play important roles in promoting cancer progression and metastasis, such as but not limited to VEGF-A, VEGF-B, VEGF-C, VEGF-D, and placental growth factor (PIGF). Thus, the design of the present bispecific antibody platform can result in targeted clearance of tumor-promoting growth factors and cytokines in the tumor microenvironments via co-phagocytosis along with the targeted cancer cells by tumor-associated macrophages (TAMs) through antibody-dependent cellular phagocytosis (ADCP) as illustrated in FIG. 1. Thereby, the bispecific antibodies can exert greater anti-tumor activity than the simple combination of two parental antibodies.

The platform can be applied to similar temporospatial co-targeting approaches using therapeutic antibodies against other cancer targets, such as a bi-specific antibody based on the anti-EGFR antibody cetuximab and bevacizumab or an angiogenesis target, such as anti-Ang2 antibody. The method could include one antibody against a cancer-associated target and another antibody against a target that is abundant in the tumor microenvironment, such as an immunomodulatory molecule.

The design of bispecific antibodies permits simultaneous binding of the bispecific antibody to two different antigens, one antigen overexpressed on the surface of targeted cancer cells and a second soluble target enriched in the tumor microenvironment, with minimal steric hindrance of binding to the two antigens and to the Fcγ receptors expressed on immune effector cells to induce antibody-dependent cell-mediated cytotoxicity (ADCC) and antibody-dependent cellular phagocytosis (ADCP) via the Fc fragment of IgG antibodies. The Fc fragment of the bispecific antibodies may include a conventional Fc fragment and an engineered Fc fragment for enhanced binding affinity to Fcγ receptors on the immune effector cells for improvement of the ADCC and ADCP effects. In some aspects, the first antibody is engineered as a single chain antibody (scFv) to be fused to the heavy chain (H) at the N-terminus of a second antibody.

Thereby, the bispecific antibodies can achieve antitumor activities not only through inducing ADCC and ADCP, but also through destroying pro-tumor cytokines or chemokines via phagocytosis through bispecific binding after ADCC and ADCP. For example, VEGFA (or similar cytokines and chemokines), produced abundantly by both cancer cells and stromal cells, not only stimulates angiogenesis but also induces immunosuppression in the tumor microenvironment. VEGFA can be effectively degraded and destroyed in the phagocytes in the tumor microenvironment via the bispecific antibody-mediated ADCC and ADCP effects as illustrated in FIG. 1.

Figures 5A, 5B:
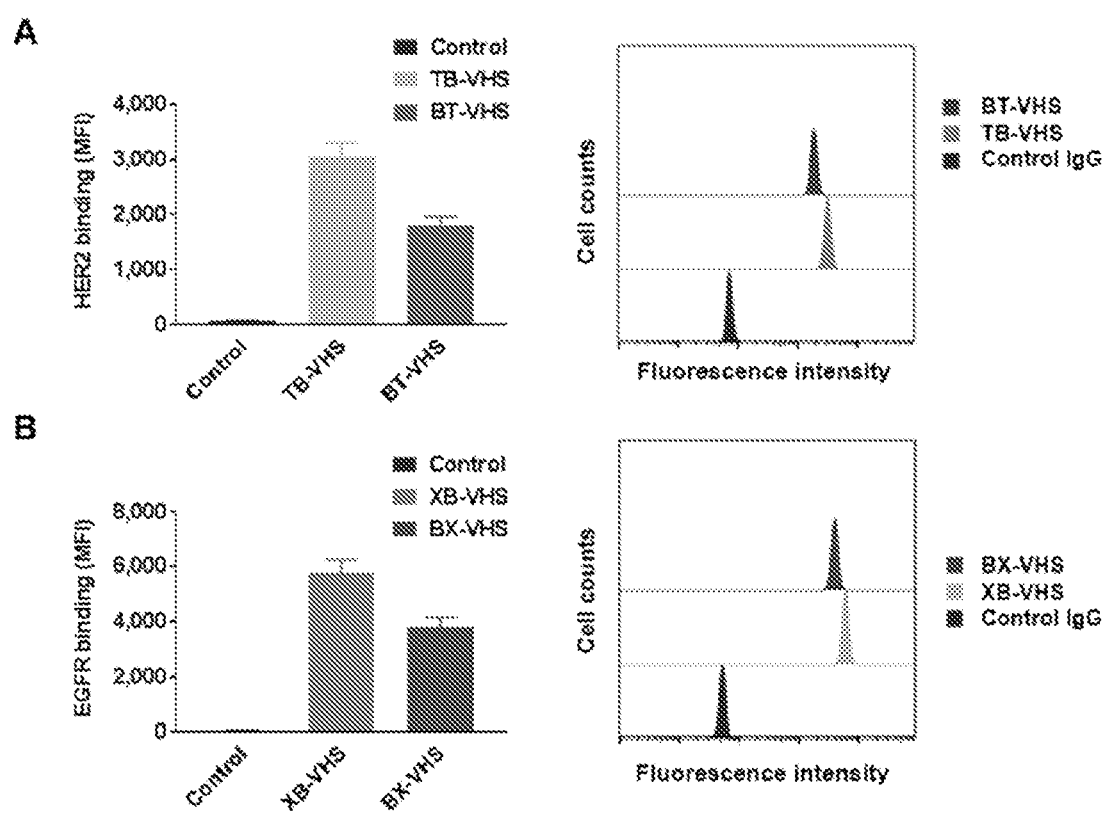
FIGS. 5A-5B: Platform comparisons between TB-VHS and BT-VHS antibodies for HER2 binding and between XB-VHS and BX-VHS antibodies for EGFR binding. HER2-overexpressing BT474 breast cancer cells (FIG. 5A) and EGFR-overexpressing HN5 head and neck cancer cells (FIG. 5B) were incubated with equal amounts (100 nM) of the indicated bispecific antibodies. Left, Medium fluorescence intensity (MFI); right; Flow cytometry diagrams.
Figures 6A, 6B:
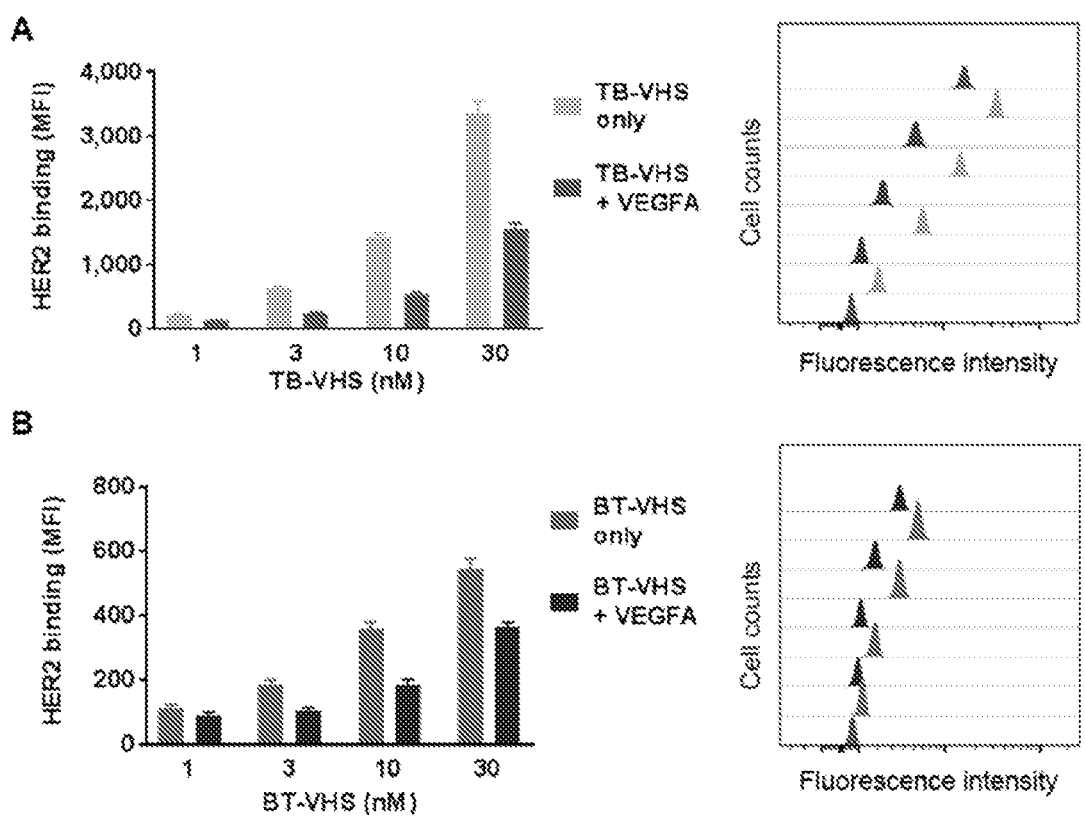
FIGS. 6A-6B: Impact of VEGFA pre-binding of the TB-VHS and BT-VHS antibodies to HER2. TB-VHS (FIG. 6A) and BT-VHS (FIG. 6B) (from 1 nM up to 30 nM) were respectively pre-mixed with fixed amounts of VEGFA. Left, Medium fluorescence intensity (MFI); right; Flow cytometry diagrams.
Figures 7A, 7B:
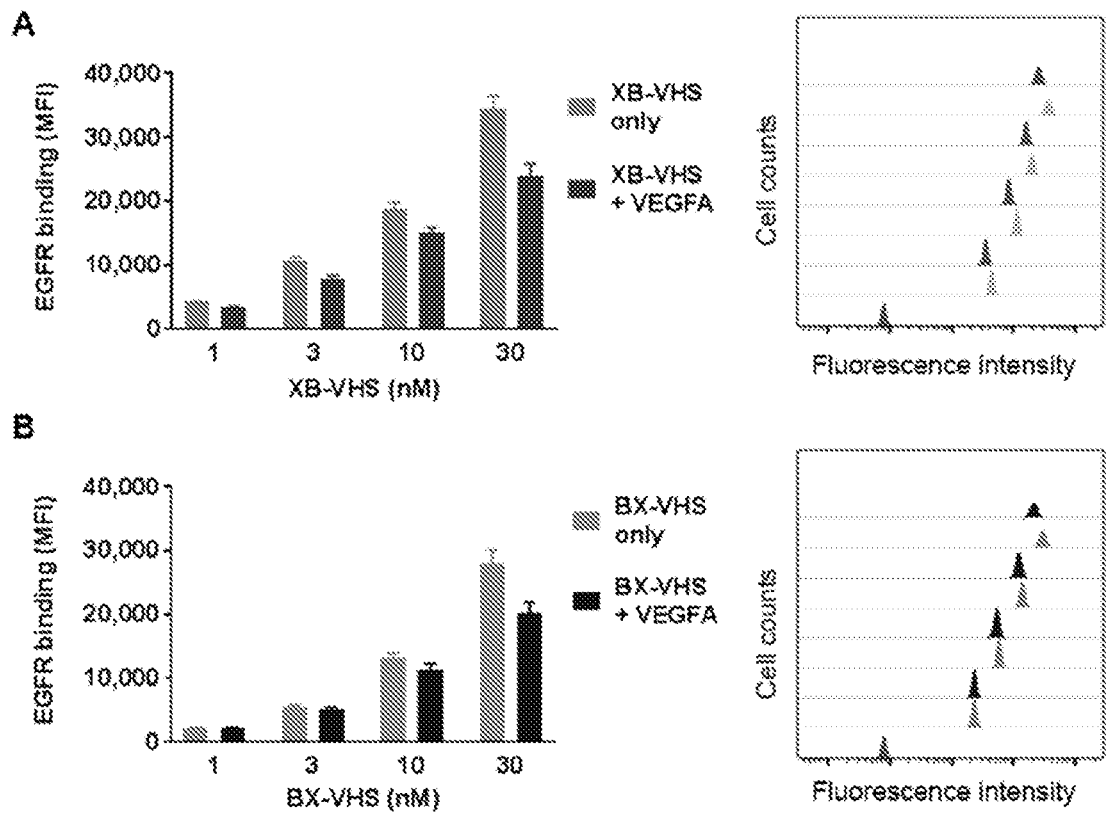
FIGS. 7A-7B: Impact of VEGFA pre-binding on the binding of XB-VHS and BX-VHS antibodies to EGFR. XB-VHS (FIG. 7A) and BX-VHX (FIG. 7B) (from 1 nM up to 30 nM) were respectively pre-mixed with or without fixed amounts of VEGFA. Left, Medium fluorescence intensity (MFI); right; Flow cytometry diagrams.

Of a special note, the present VH-modified-with-scFv (VHS) platform exhibits decreased steric hindrance for simultaneous binding of 2 antigens in close proximity, because of the relative freedom of scFv CDRs in the VHS platform. The scFv CDRs in the VHS bispecific antibody platform has easier access to antigens than the conventional CDRs in the platform, as shown in FIG. 5.

Further, the relative restriction for antigen-binding in the conventional CDR (compared to scFv CDR) in the VHS platform is harnessed strategically to permit target specificity at the tumor site, wherein the level of an intended target, such as VEGFA, is usually high due to overproduction. Thus, the VHS is able to bind to VEGFA at the tumor site due to a substantial VEGFA level, but not at normal tissue due to a low VEGFA level, thereby reducing potential toxicity of target inhibition in normal tissues (FIGS. 6-9).

Thus, the 2-in-1 temporospatial coordinated therapeutic effect of the present bispecific antibodies can provide more potent effects than the simple combination of anti-HER2 or anti-EGFR and anti-VEGFA antibodies that may lower the level of VEGFA considerably in tumor microenvironment via phagocytosis following the ADCC and ADCP effects by the bispecific antibodies.

The disclosure further provides the bispecific antibodies for VEGFA-HER2 or VEGFA-EGFR produced by this method. Accordingly, certain embodiments of the present disclosure provide bispecific antibodies with the IgG-scFv configuration (VHS platform). The variable heavy chain (VH) of the IgG is linked to the VH of the scFv. The VEGFA may be the target of IgG or the target of scFv of the configuration, thus, there are four VHS configurations provided herein including the IgG:scFv as VEGF:HER2, HER:VEGFA, VEGFA:EGFR, and EGFR:VEGFA. The VEGFA antibody may be obtained from the human anti-VEGFA antibody bevacizumab, the HER2 antibody may be obtained from the human anti-HER2 antibody trastuzumab, and the EGFR antibody may be obtained from the human anti-EGFR antibody cetuximab. Thus, the specific VHS configurations may be trastuzumab-bevacizumab (TB-VHS), bevacizumab-trastuzumab (BT-VHS), bevacizumab-cetuximab (BX-VHS), and cetuximab-bevacizumab (XB-VHS).

A VHS antibody bispecific to VEGFA and EGFR or bispecific to VEGFA and HER2 immobilizes VEGFA to the surface of EGFR- or HER2 -overexpressing cancer cells via its EGFR or HER2 binding (FIG. 1, Step 1), whereas the parental antibodies, alone or in combination, cannot do both. EGFR or HER2 binding by the bispecific antibody triggers ADCC to kill respectively targeted cancer cells through engaging immune effector cells to release perforin and granzyme B and the dead cells are then phagocytized (FIG. 1, Steps 2A & 3). NK cells, which express CD16 (FcγRIII), are the predominant type of effector cell involved in ADCC but NK cells may be scarce in the tumor microenvironment of immune "cold" tumors, which can limit patient response to cetuximab or trastuzumab. By contrast, the tumor microenvironment is rich in myeloid cells that are critical effectors of anti-cancer antibodies. ADCP is an important parallel mechanism of action mediated by binding of anti-EGFR or HER2 antibody to CD32a (FcγRII) and CD64 (FcγRI) on the myeloid cells (FIG. 1, Step 2B). Furthermore, cancer cell death by anti-EGFR or HER2 antibody-induced ADCC can stimulate neoantigen releases and facilitate DC maturation (FIG. 1, Step 4), and cross-prime CD8+ T cells to attack the cancer cells (FIG. 1, Step 5) that have escaped ADCC.

The parental antibodies may be antibodies that have been approved or are being developed for the treatment of cancer, such as HER2- or EGFR-overexpressing cancers, including cancers which are resistant to other therapies, including either of the antibodies. The treatment of cancer with a bispecific antibody provided herein can be used to deliver anti-tumor antigen activities for both tumor antigens in the same tumor microenvironment at the same time for prevention and treatment of cancer, such as metastasis of HER2-overexpressing breast cancer. These antibodies can be used to provide synergistic biological activities against cancer cell growth, invasion and metastasis. In particular, the present VHS antibodies may be used for the treatment of cancers resistant to standard therapy, such as trastuzumab (Herceptin).

I. Definitions

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. For example, a treatment may include administration of an effective amount of poziotinib or afatinib.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

The term "effective," as that term is used in the specification and/or claims, means adequate to accomplish a desired, expected, or intended result. "Effective amount," "therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

A "variant" refers to a polynucleotide or polypeptide that differs relative to a wild-type or the most prevalent form in a population of individuals by the exchange, deletion, or insertion of one or more nucleotides or amino acids, respectively. The number of nucleotides or amino acids exchanged, deleted, or inserted can be 1, 2, 3, 4, 5, 6, 7, 8, 9, 10, 11, 12, 13, 14, 15, 16, 17, 18, 19, 20 or more such as 25, 30, 35, 40, 45 or 50.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

II. VHS Antibodies

In certain embodiments, the present disclosure provides a VHS antibody platform for the production of bispecific antibodies, such as for the treatment of cancer. The VHS antibodies may have specific binding for VEGF, HER2, and/or EGFR or other combinations of tumor antigens. In particular aspects, the antibodies provided herein are IgG-scFv bispecific antibodies.

An "IgG-scFv bispecific antibody" is referred to herein as a bispecific antibody which is engineered for bispecificity by fusing two scFvs respectively to a monospecific IgG. In particular aspects, the VHS bispecific antibodies are bivalent bispecific antibodies, wherein an scFv is linked to one VH domain of IgG (see FIG. 2). Each of two identical scFvs can bind to first antigen that causes minimal steric hindrance for each of two identical IgG's VH/VL domains to bind to a second antigen simultaneously. One of the two antigens (either the first or the second antigen) may be a cell surface antigen overexpressed on cancer cells, such as HER2 and EGFR, but not limited to HER2 and EGFR. The other antigen (either the first or the second antigen) may be a tumor-associated antigen enriched in tumor microenvironment, such as VEGF but not limited to VEGF.

Bivalent bispecific antibodies are subjected to steric hindrance for simultaneous binding of 2 antigens in the CDRs of the antibody; however, the extent to which varies among different platforms. The current VHS platform provides bispecific antibodies which are minimally sterically hindered for simultaneous binding of 2 antigens when compared with other platforms, such as a "2-in-1" bispecific antibody (Bostrom et al, 2009), and can be used as more effective therapeutics, such as for cancer therapy.

The goal of a bispecific antibody is to bind 2 different targets simultaneously in a temporospatially coordinated way, rather than alternatively, in order to achieve the expected therapeutic synergisms. For example, a HER2-VEGFA bispecific antibody can bind to VEGFA and immobilize it to the surface of HER2-overexpressing cancer cells via its HER2-binding (depicted as step 1 in FIG. 1), whereas either of the parental antibodies, alone or in combination, cannot do both. HER2 binding by the bispecific antibody can trigger ADCC to kill targeted cancer cells through engaging immune effector cells to release perforin and granzyme B (i.e., step 2 and step 3 of FIG. 1).

NK cells, which exclusively express CD16 (FcγRIII), are the predominant type of effector cells involved in ADCC. However, NK cells may be scarce in the tumor microenvironment, which is known to limit patient response to trastuzumab. ADCP mediated by the myeloid cells is an important parallel mechanism of action of trastuzumab (i.e., step 2). Unlike NK cell scarcity, tumor microenvironment is rich in myeloid cells that are critical effectors of anti-cancer antibodies, although many of them promote tumor progression and metastasis. While all 3 types of the Fcγ receptor (FcγR) expressed in myeloid cells, CD32a (FcγRIIa), CD64 (FcγRI), and CD16, can participate in ADCP, CD32a is the predominant FcγR involved in this process (i.e., step 4).

Similar to new antigen release after chemotherapy, cell death via anti-HER2 antibody-induced ADCC can release new antigens and facilitate DC maturation for T cell cross-priming to attack the cancer cells which escaped from ADCC (i.e, step 5).

The antibodies according to the present disclosure may be defined, in the first instance, by binding specificity. Those of skill in the art, by assessing the binding specificity/affinity of a given antibody using techniques well known to those of skill in the art, can determine whether such antibodies fall within the scope of the instant claims. In the present application, particular binding specificities may be for VEGF and HER2 or VEGF and EGFR.

In yet another aspect, the antibodies may be defined by their variable sequence, which include additional "framework" regions. Furthermore, the antibodies sequences may vary from these sequences, optionally using methods discussed in greater detail below. For example, nucleic acid sequences may vary from those set out herein in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions.

The "variable domain" (variable domain of a light chain (VL), variable domain of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

As used herein, the term "binding" or "specifically binding" refers to the binding of the antibody to an epitope of the antigen (either human VEGF, human EGFR, or human HER2) in an in vitro assay, preferably in a plasmon resonance assay (BIAcore, GE-Healthcare Uppsala, Sweden) with purified wild-type antigen. The affinity of the binding is defined by the terms ka (rate constant for the association of the antibody from the antibody/antigen complex), $k_D$ (dissociation constant), and $K_D$ ($k_D$/ka). In one embodiment binding or specifically binding means a binding affinity ($K_D$) of $10^{-8}$ mol/L or less, in one embodiment $10^{-9}$ mol/L to $10^{-13}$ mol/L.

The antibody may comprise one or more peptide linkers, such as to link the VH and VL of the second scFv or to link the VH of the first scFv to the VH of the second scFv. The linker may be a peptide with an amino acid sequence with a length of at least 5 amino acids, such as with a length of 5 to 50 amino acids. In one embodiment said linker is (GxS)n with G=glycine, S=serine, (x=3, n=8, 9 or 10 and m=0, 1, 2 or 3) or (x=4 and n=6, 7 or 8 and m=0, 1, 2 or 3), preferably with x=4, n=6 or 7 and m=0, 1, 2 or 3, more preferably with x=4, n=7 and m=2. In one embodiment said linker is $(G_4S)_3$. GGGGSGGGGSGGGGS (SEQ ID NO:17), or ASTKGP (SEQ ID NO:18).

The term "constant region" as used within the current applications denotes the sum of the domains of an antibody other than the variable region. The constant region is not involved directly in binding of an antigen, but exhibits various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ, respectively. The light chain constant regions which can be found in all five antibody classes are called κ (kappa) and λ (lambda).

The antibodies of the present disclosure may comprise immunoglobulin constant regions derived from human origin of one or more immunoglobulin classes, wherein such immunoglobulin classes include IgG, IgM, IgA, IgD, and IgE classes and, in the case of IgG and IgA, their subclasses, especially IgG1 and IgG4.

A. VEGF

Human vascular endothelial growth factor (VEGF) is involved in the regulation of normal and abnormal angiogenesis and neovascularization associated with tumors and intraocular disorders. VEGF is a homodimeric glycoprotein that has been isolated from several sources and includes several isoforms. VEGF shows highly specific mitogenic activity for endothelial cells.

The anti-VEGF VH and VL domains of the present antibodies may be derived from anti-VEGF antibodies known in the art or may be produced by methods known in the art. Anti-VEGF antibodies include, but are not limited to, bevacizumab (Avastin) and ranibizumab (Lucentis). In some aspects, the anti-VEGF VH and VL domains of the present antibodies are derived from bevacizumab or ranibizumab, such as domains having 70%, 80%, 90%, 95%, 96%, 97%, 98%, 99%, or 100% identity or similarity to the VH and/or VL domains of bevacizumab or ranibizumab. The variable domains of anti-VEGF used herein may be optimized or humanized. In some aspects, a bispecific antibody provided herein comprises an anti-VEGF-A VH domain having at least 70%, 80%, 90%, 95%, 96%, 97%, 98%, 99%, or 100% identity or similarity to SEQ ID NO:9. In some aspects, a bispecific antibody provided herein comprises an anti-VEGF-A VL domain having at least 70%, 80%, 90%, 95%, 96%, 97%, 98%, 99%, or 100% identity or similarity to SEQ ID NO:10.

B. HER2

Human epidermal growth factor receptor-2 (HER2) is a member of human epidermal growth factor receptor (EGFR) family that stimulates various intracellular signal transduction pathways involved in cell growth control. Unlike other members of the family, HER2 has unknown ligands. HER2 is overexpressed in 20%-30% of women with breast cancer and is associated with aggressive tumor characteristics and poor prognosis.

The anti-HER2 VH and VL domains of the present antibodies may be derived from anti-HER2 antibodies known in the art or may be produced by methods known in the art. Anti-HER2 antibodies include, but are not limited to, trastuzumab (Herceptin) and pertuzumab. In some aspects, the anti-HER2 VH and VL domains of the present antibodies are derived from trastuzumab, such as domains having 70%, 80%, 90%, 95%, 96%, 97%, 98%, 99%, or 100% identity or similarity to the VH and/or VL domains of trastuzumab. The variable domains of anti-HER2 used herein may be optimized or humanized. In some aspects, a bispecific antibody provided herein comprises an anti-HER2 VH domain having at least 70%, 80%, 90%, 95%, 96%, 97%, 98%, 99%, or 100% identity or similarity to SEQ ID NO:11. In some aspects, a bispecific antibody provided herein comprises an anti-HER2 VL domain having at least 70%, 80%, 90%, 95%, 96%, 97%, 98%, 99%, or 100% identity or similarity to SEQ ID NO:12.

C. EGFR

Epidermal growth factor receptor (EGFR) is a cell membrane growth factor receptor characterized by tyrosine kinase activity that plays a crucial role in the control of key cellular transduction pathways in both normal and cancerous cells. EGFR is over-expressed in a variety of human tumors, including head and neck, breast, lung, colorectal, prostate, kidney, pancreas, ovary, brain and bladder cancer.

The anti-EGFR VH and VL domains of the present antibodies may be derived from anti-EGFR antibodies known in the art or may be produced by methods known in the art. Anti-EGFR antibodies include, but are not limited to, cetuximab (C225, Erbitux) and panitumumab. In some aspects, the anti-EGFR VH and VL domains of the present antibodies are derived from cetuximab, such as domains having 70%, 80%, 90%, 95%, 96%, 97%, 98%, 99%, or 100% identity or similarity to the VH and/or VL domains of cetuximab. The variable domains of anti-EGFR used herein may be optimized or humanized. In some aspects, a bispecific antibody provided herein comprises an anti-EGFR VH domain having at least 70%, 80%, 90%, 95%, 96%, 97%, 98%, 99%, or 100% identity or similarity to SEQ ID NO:13. In some aspects, a bispecific antibody provided herein comprises an anti-EGFR VL domain having at least 70%, 80%, 90%, 95%, 96%, 97%, 98%, 99%, or 100% identity or similarity to SEQ ID NO: 14.

D. General Antibody Production

It will be understood that antibodies binding to VEGF, HER2, and/or EGFR will have several therapeutic applications. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

In the case of human antibodies against natural pathogens, a suitable approach is to identify subjects that have been exposed to the pathogens, such as those who have been diagnosed as having contracted the disease, or those who have been vaccinated to generate protective immunity against the pathogen. Circulating anti-pathogen antibodies can be detected, and antibody producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary particular preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Quabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP) and polyoma. The recombinant expression vectors can also include origins of replication and selectable markers. Suitable selectable markers include genes that confer resistance to drugs such as G418, hygromycin or methotrexate, on a host cell into which the vector has been introduced. For example, the dihydrofolate reductase (DHFR) gene confers resistance to methotrexate and the neo gene confers resistance to G418.

Transfection of the expression vector into a host cell can be carried out using standard techniques such as electroporation, calcium-phosphate precipitation, and DEAE-dextran transfection.

Suitable mammalian host cells for expressing the antibodies, antigen binding portions, or derivatives thereof provided herein include Chinese Hamster Ovary (CHO cells), including dhfr-CHO cells, used with a DHFR selectable marker, NSO myeloma cells, COS cells and SP2 cells. In some embodiments, the expression vector is designed such that the expressed protein is secreted into the culture medium in which the host cells are grown. The antibodies, antigen binding portions, or derivatives thereof can be recovered from the culture medium using standard protein purification methods.

Antibodies of the disclosure or an antigen-binding fragment thereof can be recovered and purified from recombinant cell cultures by well-known methods including, but not limited to ammonium sulfate or ethanol precipitation, acid extraction, Protein A chromatography, Protein G chromatography, anion or cation exchange chromatography, phospho-cellulose chromatography, hydrophobic interaction chromatography, affinity chromatography, hydroxylapatite chromatography and lectin chromatography. High performance liquid chromatography ("HPLC") can also be employed for purification.

Antibodies of the present disclosure or antigen-binding fragment thereof include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present disclosure can be glycosylated or can be non-glycosylated.

Therefore an object of the present disclosure are also host cells comprising the vector or a nucleic acid molecule, whereby the host cell can be a higher eukaryotic host cell, such as a mammalian cell, a lower eukaryotic host cell, such as a yeast cell, and may be a prokaryotic cell, such as a bacterial cell.

Another object of the present disclosure is a method of using the host cell to produce an antibody and antigen binding fragments, comprising culturing the host cell under suitable conditions and recovering said antibody. Therefore, another object of the present disclosure is the antibody as described in the present disclosure produced with the host cells of the present disclosure and purified to at least 95% homogeneity by weight.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within +2 is preferred, those that are within +1 are particularly preferred, and those within +0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG1 can increase antibody dependent cell cytotoxicity, switching to class A can improve tissue distribution, and switching to class M can improve valency. Modifications in the Fc region can be introduced to extend the in vivo half-life of the antibody, or to alter Fc mediated functions such as complement activation, antibody dependent cellular cytotoxicity (ADCC), and antibody-dependent cellular phagocytosis (ADCP).

Other types of modifications include residue modification designed to reduce oxidation, aggregation, deamidation, and immunogenicity in humans. Other changes can lead to an increase in manufacturability or yield, or reduced tissue cross-reactivity in humans.

Modified antibodies may be made by any technique known to those of skill in the art, including expression through standard molecular biological techniques, or the chemical synthesis of polypeptides. Methods for recombinant expression are addressed elsewhere in this document.

E. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered.

These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

F. Engineering of Bispecific Antibodies

A wild-type IgG antibody contains two identical fragments termed "fragment, antigen binding" (or Fab), each of which is composed of the VH and CH1 domains of one heavy chain and the VL and CL domains of a light chain. Each Fab directs binding of the antibody to the same antigen. A bispecific antibody comprises an IgG antibody comprising two distinct Fabs, each of which direct binding to a separate antigen, and composed of two distinct heavy chains and two distinct light chains. The VH and CH1 domains of one heavy chain associate with the VL and CL domains of one light chain to form a "first" Fab, whereas the VH and CH1 domains of the other heavy chain associate with the VL and CL domains of the other light chain to form a "second" Fab. More particularly, the bispecific antibody may refer to an IgG1, IgG2 or IgG4 class of bi-specific antibody. Even more particular, the present bispecific antibodies are IgG1 class antibodies.

III. Methods of Use

Further provided herein are methods for treating or delaying progression of cancer in an individual comprising administering to the individual an effective amount of a bispecific antibody provided herein to a subject with cancer. The subject may have increased expression of HER2 and/or EGFR, or other cancer targets overexpressed on cancer cell surface, and/or cancer targets present in tumor microenvironment. The cancer may be metastatic, such as metastatic breast cancer.

Examples of cancers contemplated for treatment include colorectal cancer, lung cancer, head and neck cancer, breast cancer, prostate cancer, renal cancer, bladder cancer, testicular cancer, ovarian cancer, cervical cancer, pancreatic cancer, liver cancer, other gastrointestinal cancers, bone cancer, lymphomas, and pre-neoplastic lesions in these organs.

In some embodiments, the subject is a mammal, e.g., a primate, preferably a higher primate, e.g., a human (e.g., a patient having, or at risk of having, a disorder described herein). In one embodiment, the subject is in need of enhancing an immune response. In certain embodiments, the subject is, or is at risk of being, immunocompromised. For example, the subject is undergoing or has undergone a chemotherapeutic treatment and/or radiation therapy. Alternatively, or in combination, the subject is, or is at risk of being, immunocompromised as a result of an infection.

A. Formulation and Administration

The present disclosure provides pharmaceutical compositions comprising bispecific antibodies binding to VEGF and HER2, or VEGF and EGFR. Such compositions comprise a prophylactically or therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered.

Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Passive transfer of antibodies, known as artificially acquired passive immunity, generally will involve the use of intravenous or intramuscular injections. The forms of antibody can be of any source, but in particular as high-titer humanized monoclonal antibodies (MAb). Such immunity generally lasts for a certain period of time, and further administration may be required. There is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. Combination Therapies

In certain embodiments, the compositions and methods of the present embodiments involve a bispecific antibody provided herein in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

The bispecific antibody may be administered before, during, after, or in various combinations relative to an additional cancer therapy, such as immune checkpoint therapy or a macrophage-targeted therapy. The administrations may be in intervals ranging from concurrently to minutes to days to weeks. In embodiments where the poziotinib or afatinib is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below a bispecific antibody is "A" and an anti-cancer therapy is "B":

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | | B/B/A/B | A/A/B/B | | A/B/A/B | A/B/B/A | B/B/A/A |
| B/A/B/A | | B/A/A/B | A/A/A/B | | B/A/A/A | A/B/A/A | A/A/B/A |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

2. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

3. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

4. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment. As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include immune adjuvants, e.g., *Mycobacterium bovis*, *Plasmodium falciparum*, dinitrochlorobenzene, and aromatic compounds; cytokine therapy, e.g., interferons $\alpha$, $\beta$, and $\gamma$, IL-1, GM-CSF, and TNF; gene therapy, e.g., TNF, IL-1, IL-2, and p53; and monoclonal antibodies, e.g., anti-CD20, anti-ganglioside GM2, and anti-p185. It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Publication Nos. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129; International Patent Publication Nos. WO 01/14424, WO 98/42752, and WO 00/37504 (CP675,206, also known as tremelimumab; formerly ticilimumab); and U.S. Pat. No. 6,207,156 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application Nos. WO2001014424, and WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

5. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

6. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. Kits

In still further embodiments, the present disclosure concerns kits for use with the methods described above. The kits will thus comprise, in suitable container means, a bispecific antibody that binds to VEGF and HER2, or VEGF and EGFR, and optionally other reagents. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Engineering, Expression, and Bispecific Binding of VHS Antibodies

Efficacy of trastuzumab plus bevacizumab may depend on 2-in-1 temporospatially coordinated action: Preclinical studies have shown that VEGFA expression is regulated by HER2 signaling. VEGFA overexpression is correlated significantly with HER2 overexpression and HER2-induced aggressiveness of breast cancer in patients. Therefore, there is a biological rationale for combination of trastuzumab with the VEGFA antibody bevacizumab. The AVEREL trial reported in 2013 showed an influence on progression-free survival (PFS) when bevacizumab was combined with first-line trastuzumab and docetaxel in patients with HER2-overexpressing breast cancer; however, no statistically significant improvement was found in investigator-assessed PFS (Gianni et al., 2013). An independent review committee (IRC) found a PFS benefit with a similar 3-month increase in median PFS with bevacizumab, but the authors noted that "the hazard ratio [HR] for investigator-assessed PFS was 0.73 in the subgroup with measurable disease and 1.42 in the smaller group with nonmeasurable disease" and posited that "a possible interpretation of the AVEREL findings is selection of measurable lesions by the IRC".

The present studies used the VHS platform to generate recombinant antibodies bispecific for HER2 and VEGFA as well as bispecific EGFR and VEGFA. FIG. 2 shows the design of the VHS bispecific antibodies compared to a conventional antibody. The gene sequences coding for the heavy and light chains of 4 parental antibodies, trastuzumab (anti-human HER2), bevacizumab (anti-human VEGFA), and cetuximab (anti-human EGFR), were obtained from the public domain. Codon-optimized DNA fragments encoding the antibody genes were synthesized, constructed, subcloned into a home-made construct, and expressed in CHO cells. Recombinant antibodies were purified from the conditioned medium of CHO cells cultured in chemically defined serum-free medium. The trastuzumab-bevacizumab-VHS (TB-VHS) was engineered in the framework of humanized IgG1, similar to trastuzumab and bevacizumab.

Figures 4A, 4B:
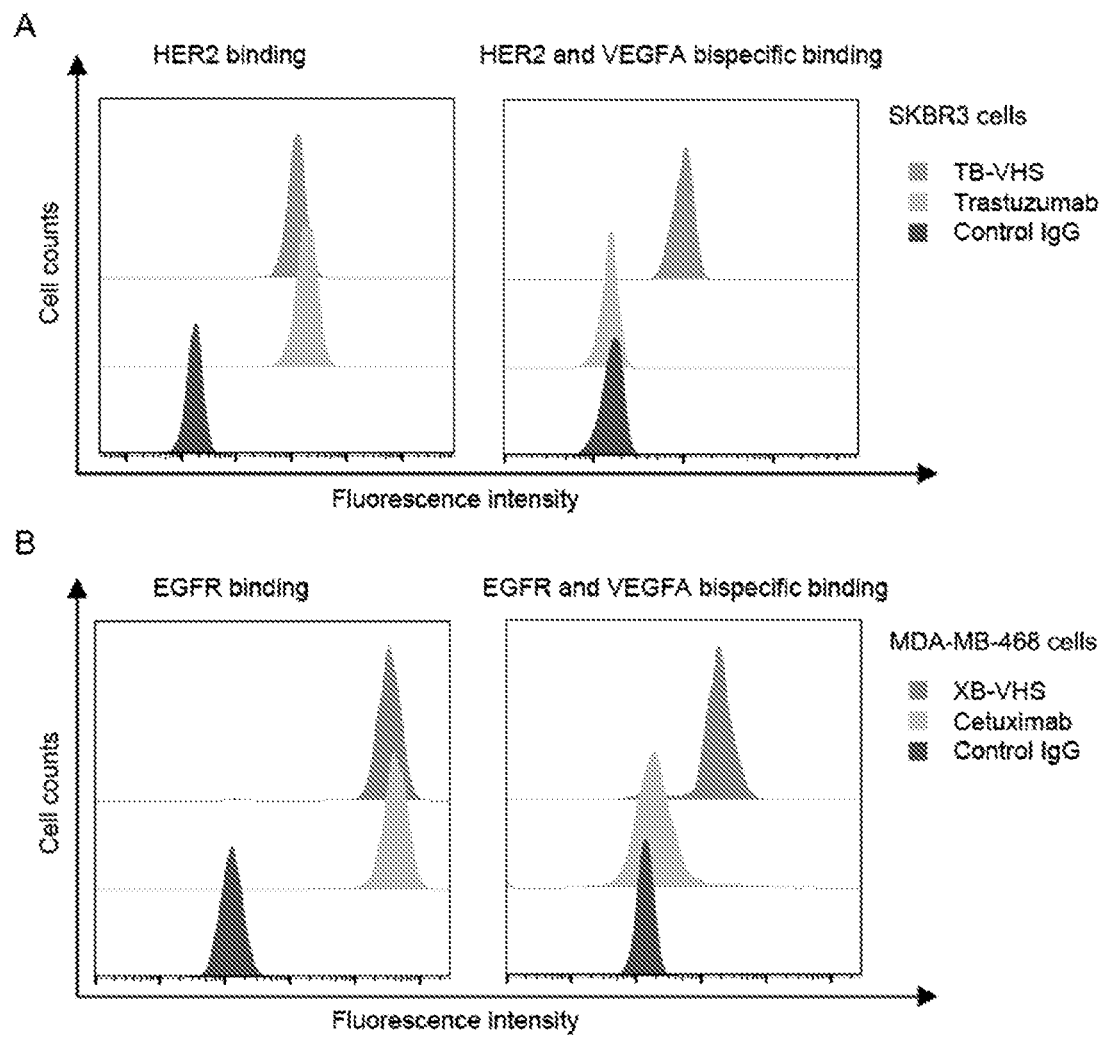
FIGS. 4A-4B: Bispecific binding to VEGFA and HER2 in HER2-overexpressing SKBR3 breast cancer cells (FIG. 4A) and bispecific binding to VEGFA and EGFR in EGFR-overexpressing MDA-MB-468 breast cancer cells (FIG. 4B). The cells were incubated with FITC-labelled anti-human IgG antibody (left panels, FIGS. 4A and 4B), or with VEGFA-GFP (right panels, FIGS. 4A and 4B).

FIG. 4 confirms bispecific binding of the TB-VHS and XB-VHS antibodies in live cells by flow cytometry analysis. SBKR3 cells (FIG. 4A) and MDA-MB-468 (FIG. 4B) were incubated with indicated antibodies (100 nM) on ice for 1 h. After cell wash to remove the unbound antibodies, the cells were incubated with FITC-labelled anti-human IgG antibody (left, FIGS. 4A and 4B), or with VEGFA-GFP fusion protein (right panel, FIGS. 4A and 4B) for an additional 45 minutes. The cell suspensions were then subjected to flow cytometry analysis to detect the level of antibodies bound to the cells. The data were processed with FlowJo. Together, these data demonstrate that TB-VHS is bispecific for HER2 and human VEGFA and XB-VHS is bispecific for EGFR and human VEGFA.

To compare the TB-VHS and BT-VHS antibodies for HER2 binding and between XB-VHS and BX-VHS antibodies for EGFR binding, HER2-overexpressing BT474 breast cancer cells (FIG. 5A) and EGFR-overexpressing HN5 head and neck cancer cells (FIG. 5B) were incubated with equal amounts (100 nM) of the indicated bispecific antibodies on ice for 1 h. After cell wash to remove the unbound antibodies, the cells were incubated with FITC-labelled anti-human IgG antibody for an additional 45 minutes. The cell suspensions were subjected to flow cytometry analysis to detect the level of antibodies bound to the cells. The data were processed with Flow-Jo software package. The data showed that both of the antibody configurations TB-VHS and BT-VHS or XB-VHS and BX-VHS have strong HER2 or EGFR binding, respectively. However, it was observed that the TB-VHS and XB-VHS antibodies, wherein the anti-VEGFA activity was constructed in the VH/VL domains in VHS platform, had stronger binding to HER2 or to EGFR, as compared to the alternate configuration (i.e., BT-VHS or BX-VHS).

Next, the impact of steric hindrance caused by VEGFA pre-binding to TB-VHS and BT-VHS antibodies on their respective binding to HER2 was determined. Varying amounts (from 1 nM up to 30 nM) of TB-VHS (FIG. 6A) and BT-VHS (FIG. 6B) were respectively pre-mixed with or without a fixed amount of VEGFA or not for 1 hour. The reactions mixtures were then incubated with HER2-overexpressing BT474 breast cancer cells on ice for 1 hour. After cell wash to remove the unbound antibodies, the cells were incubated with FITC-labelled anti-human IgG antibody for an additional 45 minutes. The cell suspensions were subjected to flow cytometry analysis to detect the level of TB-VHS or BT-VHS bound to BT474 cells through HER2 binding. The data were processed with FlowJo. It was found that, in both TB-VHS and BT-VHS configurations, their pre-incubation with VEGFA did decrease their binding to HER2; however, there was still a substantial level (~50%) of HER2 binding by TB-VHS or BT-VHS antibodies compared to the level of HER2 binding by TB-VHS or BT-VHS without VEGFA pre-binding.

Similarly, the impact of steric hindrance caused by VEGFA pre-binding to XB-VHS and BX-VHS antibodies on their respective binding to EGFR was determined. Varying amounts (from 1 nM up to 30 nM) of XB-VHS (FIG. 7A) and BX-VHS (FIG. 7B) were respectively pre-mixed with or without fixed amount of VEGFA for 1 hour. The reaction mixtures were then incubated with EGFR-overexpressing MDA-MB-468 breast cancer cells on ice for 1 hour. After cell wash to remove the unbound antibodies, the cells were incubated with FITC-labelled anti-human IgG antibody for an additional 45 minutes. The cell suspensions were subjected to flow cytometry analysis to detect the level of XB-VHS or BX-VHS bound to MDA-MB-468 cells through EGFR binding. The data were processed with FlowJo. It was found that, in both XB-VHS and BX-VHS configurations, pre-incubation with VEGFA did also decrease their binding to EGFR; however, there was still a substantial level (>50%) of EGFR binding by XB-VHS and BX-VHS antibodies compared to the level EGFR binding by XB-VHS or BX-VHS without VEGFA pre-binding.

Figure 8:
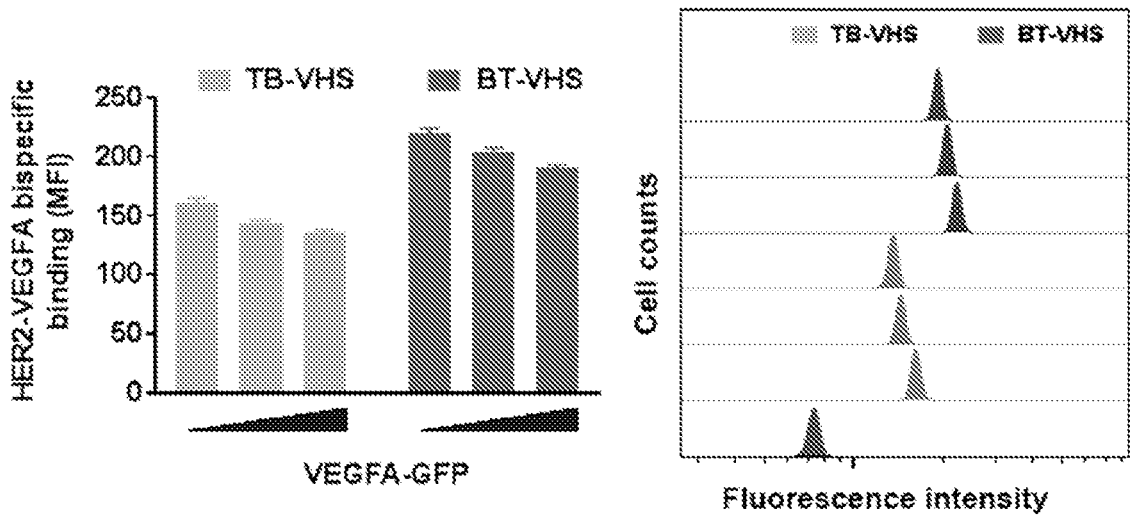
FIG. 8: Platform comparison between TB-VHS and BT-VHS antibodies for VEGFA and HER2 bispecific binding. TB-VHS and BT-VHS (100 nM) were respectively pre-mixed with 3-fold were incubated with HER2-overexpressing SKBR3 breast cancer cells. Left, Medium fluorescence intensity (MFI); right; Flow cytometry diagrams.

Platform comparison between TB-VHS and BT-VHS antibodies for VEGFA and HER2 bispecific binding was also performed when a fixed amount (100 nM) of TB-VHS and BT-VHS was respectively pre-mixed with VEGFA-GFP fusion protein at various levels (in 3-fold serial increases). The reaction mixtures were incubated with HER2-overexpressing SKBR3 breast cancer cells on ice for 1 hour. After cell wash to remove the unbound antibodies, the cell suspensions were subjected to flow cytometry analysis to detect the level of VEGFA-GFP fusion bound to SKBR3 cells through HER2 binding by TB-VHS or by BT-VHS. The data were processed with FlowJo. It was observed that the BT-VHS, wherein the anti-VEGFA activity was constructed in the scFv in the VHS platform, had stronger binding to VEGFA than TB-VHS, the alternate configuration. It was also observed that, owing to steric hindrance caused by simultaneous binding to the 2 antigens on the same antibody, the more that VEGFA-GFP binds to BT-VHS or TB-VHS antibody, the less that BT-VHS or TB-VHS antibody binds to HER2 on SKBR3 cells. Regardless, there was still a substantial level of HER2 binding in the presence of different levels of VEGFA-GFP fusion protein (FIG. 8).

Figure 9:
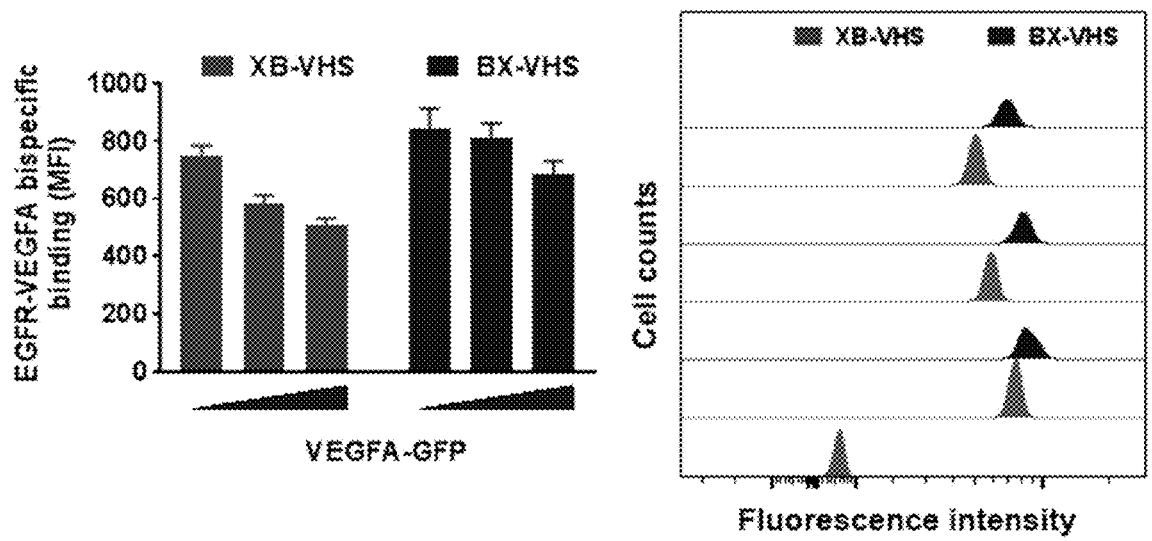
FIG. 9: Platform comparison between XB-VHS and BX-VHS antibodies for VEGFA and EGFR bispecific binding.

Platform comparison between XB-VHS and BX-VHS antibodies for VEGFA and EGFR bispecific binding was also performed when a fixed amount of XB-VHS and BX-VHS (100 nM) were respectively pre-mixed VEGFA-GFP fusion protein at various levels (in 3-fold serial increases). The reaction mixtures were incubated with EGFR-overexpressing MDA-MB-468 breast cancer cells on ice for 1 hour. After cell wash to remove the unbound antibodies, the cell suspensions were subjected to flow cytometry analysis to detect the level of VEGFA-GFP fusion bound to MDA-MB-468 cells through EGFR binding by XB-VHS or by BX-VHS. The data were processed with FlowJo. It was observed that the BX-VHS, wherein the anti-VEGFA activity was constructed in the scFv in VHS platform, had stronger binding to VEGFA than XB-VHS, the alternate configuration. It was also observed that, owing to steric hindrance caused by simultaneous binding to the 2 antigens on the same antibody, the more that VEGFA-GFP binds to BX-VHS or XB-VHS antibody, the less that BX-VHS or XB-VHS antibody binds to EGFR on MDA-MB-468 cells, but there was still a substantial level of EGFR binding in the presence of different levels of VEGFA-GFP fusion protein (FIG. 9).

As addressed in FIG. 6 to FIG. 9, binding of one antigen may interfere with binding of a second antigen when 2 relevant antigen-binding sequences in the complementarity-determining regions (CDRs) in the variable domains are too close, causing steric hindrance in the CDRs in a bispecific antibody (Bostrom et al., 2009). The impact of steric hindrance on simultaneous binding of two antigens in the VHS platform was measured stoichiometrically When 5 nM TB-VHS was incubated with 5 nM biotinylated VEGFA and increasing concentrations of HER2 extracellular domain (ECD) recombinant protein in a solution at 4° C. for 1 hour (FIG. 10A). 5 nM TB-VHS was incubated with 5 nM HER2 ECD recombinant protein and increasing concentrations of biotinylated VEGFA and unlabeled VEGFA in a solution at 4° C. for 1 hours (FIG. 10B). In both experiments, separate 96-well microplates coated with rabbit anti-human Fc antibody or HER2 ECD recombinant protein were used to capture TB-VHS. Binding of TB-VHS to VEGFA was detected by streptavidin-HRP, and binding of TB-VHS to HER2 was detected by a biotinylated anti-HER2 antibody and then streptavidin-HRP. It was shown that TB-VHS binds simultaneously to VEGFA and HER2 with only limited intramolecular steric hindrance.

Thus, by adopting the VHS platform, over 50% maximal binding of TB-VHS to VEGFA was detected in the presence of excess HER2 extracellular domain (ECD) up to 10-fold higher than VEGFA vice versa, which is remarkably better than the data reported in the literature on a 2-in-1 HER2-VEGF antibody (Bostrom et al., 2009), which showed that VEGFA binding was nearly abolished when there was an excess of HER2 binding (inset in FIG. 10). The current data show that TB-VHS can bind to VEGFA and HER2 simultaneously and that while there exists some level of intramolecular steric hindrance, this only slightly limits TB-VHS binding of a second antigen (HER2 or VEGFA).

FIG. 11 shows the physiochemical properties and functional characterization of TB-VHS. Coomassie blue-stained gels of TB-VHS and its parent antibodies were separated by SDS-PAGE under reducing (right) and non-reducing (left) conditions (FIG. 11A). Specific binding of TB-VHS and its parent antibodies to human HER2 and human VEGFA by ELISA was determined (FIG. 11B). For detecting HER2 binding, HER2 extracellular domain recombinant protein-coated 96-well microplates were used to capture the antibodies, and antibodies were detected by HRP-labelled anti-human IgG antibody. For detecting VEGFA binding, rabbit anti-human Fc-antibody-coated 96-well microplates were used to capture the antibodies, and antibodies were detected by biotinylated human VEGFA and streptavidin-HRP conjugate. TB-VHS, bevacizumab, and trastuzumab were incubated in a water bath at 50° C. for 1 hour, and then these antibodies and antibodies stored at 4° C. were subjected as in FIG. 9B (FIG. 11C). TB-VHS has a higher molecular weight than either of the conventional antibodies because of scFv fusion. The IC50 for TB-VHS binding to human VEGFA was similar to the IC50 for bevacizumab binding to VEGFA and the IC50 for TB-VHS binding to HER2 was similar to the IC50 for trastuzumab binding to HER2. There was no significant loss of TB-VHS binding affinity to VEGFA or to HER2 after incubation at 50° C. for 1 h, compared to the activity of the same antibodies stored at 4° C., indicating that the protein structure of VHS bispecific antibody is quite stable.

For comparison of the binding of TB-VHS to HER2 and VEGFA with its parental antibodies, SKBR3, and SUM190 cells were incubated with control IgG, trastuzumab, bevacizumab, or TB-VHS and then stained with FITC-labelled anti-human IgG antibody for flow cytometry analysis (FIG. 12A) and observation under fluorescent microscope (only SUM190 cells are shown) (FIG. 12B). The flow cytometry and fluorescence microscopy show TB-VHS binding to HER2-overexpressing SKBR3 and SUM190 cells in culture. A group of HER2-overepxressing and non-overexpressing breast cancer cell lines were incubated with 20 nM bevacizumab, trastuzumab, or TB-VHS on ice for 30 minutes (FIG. 12C). The cell lysates were then harvested and subjected to Western blotting with the antibodies shown at right. Western blotting detected trastuzumab and TB-VHS, but not bevacizumab, in the lysates of SKBR3 and SUM190 cells, which overexpress HER2, but not in the lysates of MDA-MB-468 and MDA-MB-231 cells, which do not express detectable HER2. Next, biotinylated VEGFA was incubated with the indicated antibodies on ice for 1 hour (FIG. 12D). The biotinylated VEGFA mixed with or without the antibodies was then incubated with HUVECs on ice for 1 hour. Cells were then washed, incubated for 30 minutes with FITC-labelled streptavidin (R&D Systems), and then subjected to flow cytometry analysis. TB-VHS and bevacizumab, but not trastuzumab, inhibited biotinylated VEGFA for binding to VEGFR in cultured human umbilical vein endothelial cells (HUVECs), which express a very high level of VEGFR.

Together, the data showed that TB-VHS binds to HER2-overexpressing breast cancer cells and inhibits VEGFA binding to HUVECs.

It was also found that TB-VHS depletes VEGFA in conditioned medium from cultures of breast cancer cells and breast fibroblasts, acting similarly to bevacizumab. Serially diluted conditioned medium from cultures of BT474 human breast cancer cells (FIG. 13A) and 1068K human breast fibroblasts (FIG. 13B) were subjected to immunodepletion by incubation with the indicated antibodies and protein-A beads for 1 hour followed by removal of the beads by centrifugation. The medium supernatant was used for detection of VEGFA by a quantitative VEGFA by a quantitative VEGFA ELISA kit (Roche). The ELISA detected no VEGFA in the conditioned medium after immunodepletion with bevacizumab or TB-VHS but a high level of VEGFA in the conditioned medium after immunodepletion with control antibody or trastuzumab.

For determination of the activity of TB-VHS to block VEGFA-induced cell signaling and function, HUVECs were untreated, treated with 150 ng/mL VEGFA for 2 minutes, or treated with 150 ng/mL VEGFA that was preincubated with control IgG, bevacizumab, TB-VHS, or trastuzumab (FIG. 14A). Cell lysates were analyzed by Western blotting with the antibodies VEGFR2-Y1175p, Akt-S473p, and Erk-T202/T204p. In FIG. 14B, HUVECs were cultured for 4 days in culture medium with or without VEGFA or in VEGFA-deficient medium supplemented with 50× concentrated conditioned medium from BT474 cell culture that was subjected to immunodepletion with the indicated antibodies by using procedures described for FIG. 13A. Cell proliferation was measured with alamarBlue assay at 570 nm. In FIG. 14 C, HUVECs ($5 \times 10^4$ cells) were seeded into the upper chamber of a Boyden chamber in 0.25 mL of medium with 0.75 mL of culture medium without (control) or with VEGFA, or the VEGFA in the medium was subjected to immunodepletion. Migration of HUVECS through the transwell membrane in the chamber was measured after 24 hours. It was found that TB-VHS inhibits VEGFA-induced activation of cell signaling and VEGFA-induced proliferation and migration in HUVECs, acting similarly to bevacizumab.

For determination of the activity of TB-VHS to block HER2-mediated cell signaling and function, two HER2-overexpressing breast cancer cell lines, SUM190 and SKBR3, were treated as shown in FIG. 15. SKBR3 breast cancer cells were untreated or treated with bevacizumab, trastuzumab, or TB-VHS for 24 hours (FIG. 15A). It was found that TB-VHS and trastuzumab, but not bevacizumab, inhibited phosphorylation of HER2-Y877 and phosphorylation of HER2 downstream substrates Akt-S473 and Erk-T202/Y204 in SKBR3 cells. In FIG. 15B, SUM190 and SKBR3 cells were treated with antibodies as indicated for 4 days. TB-VHS and trastuzumab inhibited proliferation of SKBR3 and SUM190 cells, but with a less than 50% proliferation inhibition after 4-5 days of treatment in culture, which cannot fully explain the remarkable antitumor activity of trastuzumab seen in patients. In FIG. 15C, SKBR3 cells were treated with antibodies as indicated for 4 days in normoxia (N, 21% O2) or in a hypoxia chamber (H, 1% O2). It was found that SKBR3 cells grew more slowly inside a hypoxia chamber than in normoxia; however, their response rate (after normalization) to trastuzumab- and TB-VHS-induced growth inhibition was similar in hypoxia and normoxic culture. In FIGS. 15D and E, SKBR3 cells were untreated or treated with antibodies shown at top for 24 hours under normoxia or hypoxia. Interestingly, it was found that VEGFR2 expression was induced in SKBR3 cells under hypoxia. Although the level of VEGFR2 upregulation was small compared to the level of VEGFR in HUVECs, this finding does suggest that VEGFA may act on breast cancer cells in addition to acting on stromal cells. It was further found that the increase in HIF-1α by hypoxia was strongly inhibited by trastuzumab and TB-VHS, whereas bevacizumab slightly upregulated HIF-1α, possibly because of feedback regulation as a result of VEGFA inhibition by bevacizumab.

In FIG. 15F, SUM190 and SKBR3 cells were labeled with Calcein and then mixed with NK cells from healthy donors at the indicated effector/target ratios. After 4 hours incubated with the indicated antibodies at 37° C., the percentage of cells killed was measured by the amount of Calcein released by the formula [(test release-spontaneous release)/(maximum release-spontaneous release)×100. Rituximab was used as an isotype control antibody. It was found that TB-VHS induced ADCC in SKBR3 and SUM190 cells at a level similar to that induced by trastuzumab, which was reported in literature (Barok et al., 2007; Prang et al., 2005; Collins et al., 2012).

In FIG. 16, BT474 breast cancer cells labeled with eFluor 670 cell proliferation marker were phagocytized by RAW264.7 macrophages when cells were co-cultured in the presence of trastuzumab, TB-VHS, or TG-VHS but not in the presence of bevacizumab, G6.31, or control antibody (FIG. 16A). Addition of VEGFA-GFP fusion protein in the co-culture resulted in co-engulfment of VEGFA-GFP into the RAW264.7 macrophages engaged by TB-VHS or TG-VHS but not the RAW264.7 macrophages engaged by trastuzumab, as detected by multicolor FACS (FIG. 16B). Therefore, TB-VHS and TG-VHS induce ADCP and co-phagocytosis of VEGFA-GFP along with BT474 breast cancer cells in co-cultures of BT474 cells and RAW264.7 macrophages, acting differently from trastuzumab.

A pilot in vivo experiment was performed to evaluate the effect of TB-VHS on survival in nude mice implanted with 4T1 cells transduced to overexpress human HER2 (4T1/HER2). The 4T1/HER2 cells were implanted into the mammary fat pads of nude mice along with mouse fibroblasts transduced to express and secrete human VEGFA. The 4T1 model was used because 4T1 is one of the most aggressive mouse mammary tumor models that can metastasize and kill mice. Nude mice were used because human HER2 and human VEGFA, to which TB-VHS targets via the activities inherited from trastuzumab and bevacizumab, would be immunogenic in normal mice. Treatment started on day 4 after tumor cell implantation. The mice started dying on day 12 after tumor cell implantation. IVIS imaging detected massive metastasis on day 20. Compared to the massive metastasis in mice untreated or treated with bevacizumab, trastuzumab, alone or in simple combination, the extent of metastasis in TB-VHS-treated mice was less (FIG. 17A). An encouraging survival advantage was observed after TB-VHS treatment compared to simple combination of trastuzumab and bevacizumab. By day 32 when all mice in other groups died, there were 4 of 8 mice treated with TB-VHS remained alive (FIG. 17B), despite the facts that 2 major factors may have limited the therapeutic effect of TB-VHS in the mouse model (lack of participation of host adaptive immune response and the effect of inhibition of host-derived VEGFA because TB-VHS cannot inhibit mouse stromal cell-derived VEGFA).

In patients, TB-VHS is expected to inhibit both cancer cell-derived and stromal cell-derived VEGFA because they are all human VEGFA, and unlike the preclinical experiment models with immunocompromised mice, the immunity in cancer patients, although may be reduced, is not completely compromised. Therefore, the antitumor activity of TB-VHS will not be limited by the factors seen with preclinical mouse models. Thus, the VHS bispecific antibodies provided herein can be used as improved therapeutics for cancer patients.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Barok et al., *Mol Cancer Ther* 6:2065-72, 2007.
Bostromet et al., *Science* 323:1610-4, 2009.
Collins et al., *Ann Oncol* 23:1788-95, 2012.
Gianni et al., *J Clin Oncol* 31:1719-25, 2013.
International Patent Publication No. WO 00/37504
International Patent Publication No. WO 01/14424
International Patent Publication No. WO 98/42752
International Patent Publication No. WO1995001994
International Patent Publication No. WO1998042752
International Patent Publication No. WO2000037504
International Patent Publication No. WO2001014424
International Patent Publication No. WO2006/121168
International Patent Publication No. WO2009/101611
International Patent Publication No. WO2009/114335
International Patent Publication No. WO2010/027827
International Patent Publication No. WO2011/066342
International Patent Publication No. WO2015016718
Pardoll, *Nat Rev Cancer*, 12(4): 252-64, 2012.
Park S, Jiang Z, Mortenson E D, Deng L, Radkevich-Brown O, Yang X, Sattar H, Wang Y, Prang et al., *Br J Cancer* 92:342-9, 2005.
U.S. Pat. No. 4,680,338
U.S. Pat. No. 4,870,287
U.S. Pat. No. 5,141,648
U.S. Pat. No. 5,563,250
U.S. Pat. No. 5,760,395
U.S. Pat. No. 5,844,905
U.S. Pat. No. 5,856,456
U.S. Pat. No. 5,880,270
U.S. Pat. No. 5,885,796
U.S. Pat. No. 6,207,156
U.S. Pat. No. 8,008,449
U.S. Pat. No. 8,017,114
U.S. Pat. No. 8,119,129;
U.S. Pat. No. 8,329,867
U.S. Pat. No. 8,354,509
U.S. Pat. No. 8,735,553
U.S. Patent Publication No. US20110008369
U.S. Patent Publication No. US2014022021
U.S. Patent Publication No. US20140294898

What is claimed is:

1. A bispecific antibody comprising an anti-human vascular endothelial growth factor (VEGF) IgG antibody linked to an anti-human epidermal growth factor receptor-2 (HER2) scFv, wherein the VH domain of the IgG antibody is linked to the VH domain of the scFv, wherein the bispecific antibody comprises a first domain comprising SEQ ID NO:3 and a second domain comprising SEQ ID NO:4.

2. A pharmaceutical composition comprising the bispecific antibody of claim 1 and a pharmaceutically acceptable carrier.

3. A method of treating cancer in a subject having a HER2-overexpressing cancer comprising administering the bispecific antibody of claim 1 to the subject.

4. The method of claim 3, wherein the cancer is breast, head and neck, lung, colorectal, prostate, kidney, pancreas, ovary, brain or bladder cancer.

* * * * *

SEQUENCE LISTING

```
<160> NUMBER OF SEQ ID NOS: 18

<210> SEQ ID NO 1
<211> LENGTH: 701
<212> TYPE: PRT
<213> ORGANISM: Artificial sequence
<220> FEATURE:
<223> OTHER INFORMATION: Synthetic amino acid

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
```

-continued

```
            115                 120                 125
Ser Gly Gly Gly Leu Val Gln Pro Gly Gly Ser Leu Arg Leu Ser Cys
            130                 135                 140
Ala Ala Ser Gly Tyr Thr Phe Thr Asn Tyr Gly Met Asn Trp Val Arg
145                 150                 155                 160
Gln Ala Pro Gly Lys Gly Leu Glu Trp Val Gly Trp Ile Asn Thr Tyr
                    165                 170                 175
Thr Gly Glu Pro Thr Tyr Ala Ala Asp Phe Lys Arg Arg Phe Thr Phe
                180                 185                 190
Ser Leu Asp Thr Ser Lys Ser Thr Ala Tyr Leu Gln Met Asn Ser Leu
            195                 200                 205
Arg Ala Glu Asp Thr Ala Val Tyr Tyr Cys Ala Lys Tyr Pro His Tyr
        210                 215                 220
Tyr Gly Ser Ser His Trp Tyr Phe Asp Val Trp Gly Gln Gly Thr Leu
225                 230                 235                 240
Val Thr Val Ser Ser Ala Ser Thr Lys Gly Pro Glu Val Gln Leu Val
                245                 250                 255
Glu Ser Gly Gly Gly Leu Val Gln Pro Gly Gly Ser Leu Arg Leu Ser
                260                 265                 270
Cys Ala Ala Ser Gly Phe Asn Ile Lys Asp Thr Tyr Ile His Trp Val
            275                 280                 285
Arg Gln Ala Pro Gly Lys Gly Leu Glu Trp Val Ala Arg Ile Tyr Pro
        290                 295                 300
Thr Asn Gly Tyr Thr Arg Tyr Ala Asp Ser Val Lys Gly Arg Phe Thr
305                 310                 315                 320
Ile Ser Ala Asp Thr Ser Lys Asn Thr Ala Tyr Leu Gln Met Asn Ser
                325                 330                 335
Leu Arg Ala Glu Asp Thr Ala Val Tyr Tyr Cys Ser Arg Trp Gly Gly
                340                 345                 350
Asp Gly Phe Tyr Ala Met Asp Tyr Trp Gly Gln Gly Thr Leu Val Thr
            355                 360                 365
Val Ser Ser Ala Ser Thr Lys Gly Pro Ser Val Phe Pro Leu Ala Pro
        370                 375                 380
Ser Ser Lys Ser Thr Ser Gly Gly Thr Ala Ala Leu Gly Cys Leu Val
385                 390                 395                 400
Lys Asp Tyr Phe Pro Glu Pro Val Thr Val Ser Trp Asn Ser Gly Ala
                405                 410                 415
Leu Thr Ser Gly Val His Thr Phe Pro Ala Val Leu Gln Ser Ser Gly
                420                 425                 430
Leu Tyr Ser Leu Ser Ser Val Val Thr Val Pro Ser Ser Ser Leu Gly
            435                 440                 445
Thr Gln Thr Tyr Ile Cys Asn Val Asn His Lys Pro Ser Asn Thr Lys
        450                 455                 460
Val Asp Lys Lys Val Glu Pro Lys Ser Cys Asp Lys Thr His Thr Cys
465                 470                 475                 480
Pro Pro Cys Pro Ala Pro Glu Leu Leu Gly Gly Pro Ser Val Phe Leu
                485                 490                 495
Phe Pro Pro Lys Pro Lys Asp Thr Leu Met Ile Ser Arg Thr Pro Glu
                500                 505                 510
Val Thr Cys Val Val Val Asp Val Ser His Glu Asp Pro Glu Val Lys
            515                 520                 525
Phe Asn Trp Tyr Val Asp Gly Val Glu Val His Asn Ala Lys Thr Lys
        530                 535                 540
```

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
            565                 570                 575

Val Ser Asn Lys Ala Leu Pro Ala Pro Ile Glu Lys Thr Ile Ser Lys
        580                 585                 590

Ala Lys Gly Gln Pro Arg Glu Pro Gln Val Tyr Thr Leu Pro Pro Ser
    595                 600                 605

Arg Glu Glu Met Thr Lys Asn Gln Val Ser Leu Thr Cys Leu Val Lys
610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
            645                 650                 655

Ser Phe Phe Leu Tyr Ser Lys Leu Thr Val Asp Lys Ser Arg Trp Gln
        660                 665                 670

Gln Gly Asn Val Phe Ser Cys Ser Val Met His Glu Ala Leu His Asn
    675                 680                 685

His Tyr Thr Gln Lys Ser Leu Ser Leu Ser Pro Gly Lys
690                 695                 700

<210> SEQ ID NO 2
<211> LENGTH: 214
<212> TYPE: PRT
<213> ORGANISM: Artificial sequence
<220> FEATURE:
<223> OTHER INFORMATION: Synthetic amino acid

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

```
Phe Asn Arg Gly Glu Cys
    210

<210> SEQ ID NO 3
<211> LENGTH: 701
<212> TYPE: PRT
<213> ORGANISM: Artificial sequence
<220> FEATURE:
<223> OTHER INFORMATION: Synthetic amino acid

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser Ala Ser Thr Lys Gly Pro Glu Val Gln Leu Val Glu Ser Gly
                245                 250                 255

Gly Gly Leu Val Gln Pro Gly Gly Ser Leu Arg Leu Ser Cys Ala Ala
            260                 265                 270

Ser Gly Tyr Thr Phe Thr Asn Tyr Gly Met Asn Trp Val Arg Gln Ala
        275                 280                 285

Pro Gly Lys Gly Leu Glu Trp Val Gly Trp Ile Asn Thr Tyr Thr Gly
    290                 295                 300

Glu Pro Thr Tyr Ala Ala Asp Phe Lys Arg Arg Phe Thr Phe Ser Leu
305                 310                 315                 320

Asp Thr Ser Lys Ser Thr Ala Tyr Leu Gln Met Asn Ser Leu Arg Ala
                325                 330                 335

Glu Asp Thr Ala Val Tyr Tyr Cys Ala Lys Tyr Pro His Tyr Tyr Gly
            340                 345                 350
```

```
Ser Ser His Trp Tyr Phe Asp Val Trp Gly Gln Gly Thr Leu Val Thr
        355                 360                 365

Val Ser Ser Ala Ser Thr Lys Gly Pro Ser Val Phe Pro Leu Ala Pro
370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
                405                 410                 415

Leu Thr Ser Gly Val His Thr Phe Pro Ala Val Leu Gln Ser Ser Gly
            420                 425                 430

Leu Tyr Ser Leu Ser Ser Val Val Thr Val Pro Ser Ser Ser Leu Gly
        435                 440                 445

Thr Gln Thr Tyr Ile Cys Asn Val Asn His Lys Pro Ser Asn Thr Lys
    450                 455                 460

Val Asp Lys Lys Val Glu Pro Lys Ser Cys Asp Lys Thr His Thr Cys
465                 470                 475                 480

Pro Pro Cys Pro Ala Pro Glu Leu Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
        515                 520                 525

Phe Asn Trp Tyr Val Asp Gly Val Glu Val His Asn Ala Lys Thr Lys
    530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
        595                 600                 605

Arg Glu Glu Met Thr Lys Asn Gln Val Ser Leu Thr Cys Leu Val Lys
    610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
        675                 680                 685

His Tyr Thr Gln Lys Ser Leu Ser Leu Ser Pro Gly Lys
    690                 695                 700

<210> SEQ ID NO 4
<211> LENGTH: 214
<212> TYPE: PRT
<213> ORGANISM: Artificial sequence
<220> FEATURE:
<223> OTHER INFORMATION: Synthetic amino acid

<400> SEQUENCE: 4

Asp Ile Gln Met Thr Gln Ser Pro Ser Ser Leu Ser Ala Ser Val Gly
1               5                   10                  15
```

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
         35                  40                  45

Tyr Phe Thr Ser Ser Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 700
<212> TYPE: PRT
<213> ORGANISM: Artificial sequence
<220> FEATURE:
<223> OTHER INFORMATION: Synthetic amino acid

<400> SEQUENCE: 5

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
         35                  40                  45

Lys Tyr Ala Ser Glu Ser Ile Ser Gly Ile Pro Ser Arg Phe Ser Gly
     50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Gly Gly Gly Gly Ser
            100                 105                 110

Gly Gly Gly Gly Ser Gly Gly Gly Ser Gln Val Gln Leu Lys Gln
        115                 120                 125

Ser Gly Pro Gly Leu Val Gln Pro Ser Gln Ser Leu Ser Ile Thr Cys
130                 135                 140

Thr Val Ser Gly Phe Ser Leu Thr Asn Tyr Gly Val His Trp Val Arg
145                 150                 155                 160

```
Gln Ser Pro Gly Lys Gly Leu Glu Trp Leu Gly Val Ile Trp Ser Gly
                165                 170                 175
Gly Asn Thr Asp Tyr Asn Thr Pro Phe Thr Ser Arg Leu Ser Ile Asn
            180                 185                 190
Lys Asp Asn Ser Lys Ser Gln Val Phe Phe Lys Met Asn Ser Leu Gln
        195                 200                 205
Ser Asn Asp Thr Ala Ile Tyr Tyr Cys Ala Arg Ala Leu Thr Tyr Tyr
    210                 215                 220
Asp Tyr Glu Phe Ala Tyr Trp Gly Gln Gly Thr Leu Val Thr Val Ser
225                 230                 235                 240
Ala Ala Ser Thr Lys Gly Pro Glu Val Gln Leu Val Glu Ser Gly Gly
                245                 250                 255
Gly Leu Val Gln Pro Gly Gly Ser Leu Arg Leu Ser Cys Ala Ala Ser
            260                 265                 270
Gly Tyr Thr Phe Thr Asn Tyr Gly Met Asn Trp Val Arg Gln Ala Pro
        275                 280                 285
Gly Lys Gly Leu Glu Trp Val Gly Trp Ile Asn Thr Tyr Thr Gly Glu
    290                 295                 300
Pro Thr Tyr Ala Ala Asp Phe Lys Arg Arg Phe Thr Phe Ser Leu Asp
305                 310                 315                 320
Thr Ser Lys Ser Thr Ala Tyr Leu Gln Met Asn Ser Leu Arg Ala Glu
                325                 330                 335
Asp Thr Ala Val Tyr Tyr Cys Ala Lys Tyr Pro His Tyr Tyr Gly Ser
            340                 345                 350
Ser His Trp Tyr Phe Asp Val Trp Gly Gln Gly Thr Leu Val Thr Val
        355                 360                 365
Ser Ser Ala Ser Thr Lys Gly Pro Ser Val Phe Pro Leu Ala Pro Ser
    370                 375                 380
Ser Lys Ser Thr Ser Gly Gly Thr Ala Ala Leu Gly Cys Leu Val Lys
385                 390                 395                 400
Asp Tyr Phe Pro Glu Pro Val Thr Val Ser Trp Asn Ser Gly Ala Leu
                405                 410                 415
Thr Ser Gly Val His Thr Phe Pro Ala Val Leu Gln Ser Ser Gly Leu
            420                 425                 430
Tyr Ser Leu Ser Ser Val Val Thr Val Pro Ser Ser Ser Leu Gly Thr
        435                 440                 445
Gln Thr Tyr Ile Cys Asn Val Asn His Lys Pro Ser Asn Thr Lys Val
    450                 455                 460
Asp Lys Lys Val Glu Pro Lys Ser Cys Asp Lys Thr His Thr Cys Pro
465                 470                 475                 480
Pro Cys Pro Ala Pro Glu Leu Leu Gly Gly Pro Ser Val Phe Leu Phe
                485                 490                 495
Pro Pro Lys Pro Lys Asp Thr Leu Met Ile Ser Arg Thr Pro Glu Val
            500                 505                 510
Thr Cys Val Val Val Asp Val Ser His Glu Asp Pro Glu Val Lys Phe
        515                 520                 525
Asn Trp Tyr Val Asp Gly Val Glu Val His Asn Ala Lys Thr Lys Pro
    530                 535                 540
Arg Glu Glu Gln Tyr Asn Ser Thr Tyr Arg Val Val Ser Val Leu Thr
545                 550                 555                 560
Val Leu His Gln Asp Trp Leu Asn Gly Lys Glu Tyr Lys Cys Lys Val
                565                 570                 575
```

```
Ser Asn Lys Ala Leu Pro Ala Pro Ile Glu Lys Thr Ile Ser Lys Ala
                580                 585                 590

Lys Gly Gln Pro Arg Glu Pro Gln Val Tyr Thr Leu Pro Pro Ser Arg
            595                 600                 605

Glu Glu Met Thr Lys Asn Gln Val Ser Leu Thr Cys Leu Val Lys Gly
        610                 615                 620

Phe Tyr Pro Ser Asp Ile Ala Val Glu Trp Glu Ser Asn Gly Gln Pro
625                 630                 635                 640

Glu Asn Asn Tyr Lys Thr Thr Pro Pro Val Leu Asp Ser Asp Gly Ser
                645                 650                 655

Phe Phe Leu Tyr Ser Lys Leu Thr Val Asp Lys Ser Arg Trp Gln Gln
            660                 665                 670

Gly Asn Val Phe Ser Cys Ser Val Met His Glu Ala Leu His Asn His
        675                 680                 685

Tyr Thr Gln Lys Ser Leu Ser Leu Ser Pro Gly Lys
                690                 695                 700

<210> SEQ ID NO 6
<211> LENGTH: 214
<212> TYPE: PRT
<213> ORGANISM: Artificial sequence
<220> FEATURE:
<223> OTHER INFORMATION: Synthetic amino acid

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 700
```

```
<212> TYPE: PRT
<213> ORGANISM: Artificial sequence
<220> FEATURE:
<223> OTHER INFORMATION: Synthetic amino acid

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Tyr Thr Phe Thr Asn Tyr Gly Met Asn Trp Val Arg
145                 150                 155                 160

Gln Ala Pro Gly Lys Gly Leu Glu Trp Val Gly Trp Ile Asn Thr Tyr
            165                 170                 175

Thr Gly Glu Pro Thr Tyr Ala Ala Asp Phe Lys Arg Arg Phe Thr Phe
        180                 185                 190

Ser Leu Asp Thr Ser Lys Ser Thr Ala Tyr Leu Gln Met Asn Ser Leu
    195                 200                 205

Arg Ala Glu Asp Thr Ala Val Tyr Tyr Cys Ala Lys Tyr Pro His Tyr
210                 215                 220

Tyr Gly Ser Ser His Trp Tyr Phe Asp Val Trp Gly Gln Gly Thr Leu
225                 230                 235                 240

Val Thr Val Ser Ser Ala Ser Thr Lys Gly Pro Gln Val Gln Leu Lys
            245                 250                 255

Gln Ser Gly Pro Gly Leu Val Gln Pro Ser Gln Ser Leu Ser Ile Thr
        260                 265                 270

Cys Thr Val Ser Gly Phe Ser Leu Thr Asn Tyr Gly Val His Trp Val
    275                 280                 285

Arg Gln Ser Pro Gly Lys Gly Leu Glu Trp Leu Gly Val Ile Trp Ser
290                 295                 300

Gly Gly Asn Thr Asp Tyr Asn Thr Pro Phe Thr Ser Arg Leu Ser Ile
305                 310                 315                 320

Asn Lys Asp Asn Ser Lys Ser Gln Val Phe Phe Lys Met Asn Ser Leu
            325                 330                 335

Gln Ser Asn Asp Thr Ala Ile Tyr Tyr Cys Ala Arg Ala Leu Thr Tyr
        340                 345                 350

Tyr Asp Tyr Glu Phe Ala Tyr Trp Gly Gln Gly Thr Leu Val Thr Val
    355                 360                 365

Ser Ala Ala Ser Thr Lys Gly Pro Ser Val Phe Pro Leu Ala Pro Ser
370                 375                 380
```

```
Ser Lys Ser Thr Ser Gly Gly Thr Ala Ala Leu Gly Cys Leu Val Lys
385                 390                 395                 400

Asp Tyr Phe Pro Glu Pro Val Thr Val Ser Trp Asn Ser Gly Ala Leu
            405                 410                 415

Thr Ser Gly Val His Thr Phe Pro Ala Val Leu Gln Ser Ser Gly Leu
        420                 425                 430

Tyr Ser Leu Ser Ser Val Val Thr Val Pro Ser Ser Ser Leu Gly Thr
    435                 440                 445

Gln Thr Tyr Ile Cys Asn Val Asn His Lys Pro Ser Asn Thr Lys Val
450                 455                 460

Asp Lys Lys Val Glu Pro Lys Ser Cys Asp Lys Thr His Thr Cys Pro
465                 470                 475                 480

Pro Cys Pro Ala Pro Glu Leu Leu Gly Gly Pro Ser Val Phe Leu Phe
            485                 490                 495

Pro Pro Lys Pro Lys Asp Thr Leu Met Ile Ser Arg Thr Pro Glu Val
        500                 505                 510

Thr Cys Val Val Val Asp Val Ser His Glu Asp Pro Glu Val Lys Phe
    515                 520                 525

Asn Trp Tyr Val Asp Gly Val Glu Val His Asn Ala Lys Thr Lys Pro
530                 535                 540

Arg Glu Glu Gln Tyr Asn Ser Thr Tyr Arg Val Val Ser Val Leu Thr
545                 550                 555                 560

Val Leu His Gln Asp Trp Leu Asn Gly Lys Glu Tyr Lys Cys Lys Val
            565                 570                 575

Ser Asn Lys Ala Leu Pro Ala Pro Ile Glu Lys Thr Ile Ser Lys Ala
        580                 585                 590

Lys Gly Gln Pro Arg Glu Pro Gln Val Tyr Thr Leu Pro Pro Ser Arg
    595                 600                 605

Glu Glu Met Thr Lys Asn Gln Val Ser Leu Thr Cys Leu Val Lys Gly
610                 615                 620

Phe Tyr Pro Ser Asp Ile Ala Val Glu Trp Ser Asn Gly Gln Pro
625                 630                 635                 640

Glu Asn Asn Tyr Lys Thr Thr Pro Pro Val Leu Asp Ser Asp Gly Ser
            645                 650                 655

Phe Phe Leu Tyr Ser Lys Leu Thr Val Asp Lys Ser Arg Trp Gln Gln
        660                 665                 670

Gly Asn Val Phe Ser Cys Ser Val Met His Glu Ala Leu His Asn His
    675                 680                 685

Tyr Thr Gln Lys Ser Leu Ser Leu Ser Pro Gly Lys
690                 695                 700
```

<210> SEQ ID NO 8
<211> LENGTH: 214
<212> TYPE: PRT
<213> ORGANISM: Artificial sequence
<220> FEATURE:
<223> OTHER INFORMATION: Synthetic amino acid

<400> SEQUENCE: 8

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45
```

Lys Tyr Ala Ser Glu Ser Ile Ser Gly Ile Pro Ser Arg Phe Ser Gly
            50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 9
<211> LENGTH: 123
<212> TYPE: PRT
<213> ORGANISM: Artificial sequence
<220> FEATURE:
<223> OTHER INFORMATION: Synthetic amino acid

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 10
<211> LENGTH: 107
<212> TYPE: PRT
<213> ORGANISM: Artificial sequence
<220> FEATURE:
<223> OTHER INFORMATION: Synthetic amino acid

<400> SEQUENCE: 10

Asp Ile Gln Met Thr Gln Ser Pro Ser Ser Leu Ser Ala Ser Val Gly
1               5                   10                  15

```
Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 11
<211> LENGTH: 120
<212> TYPE: PRT
<213> ORGANISM: Artificial sequence
<220> FEATURE:
<223> OTHER INFORMATION: Synthetic amino acid

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 12
<211> LENGTH: 107
<212> TYPE: PRT
<213> ORGANISM: Artificial sequence
<220> FEATURE:
<223> OTHER INFORMATION: Synthetic amino acid

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
```

```
                    85                  90                  95

Thr Phe Gly Gln Gly Thr Lys Val Glu Ile Lys
                100                 105

<210> SEQ ID NO 13
<211> LENGTH: 119
<212> TYPE: PRT
<213> ORGANISM: Artificial sequence
<220> FEATURE:
<223> OTHER INFORMATION: Synthetic amino acid

<400> SEQUENCE: 13

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ala
        115

<210> SEQ ID NO 14
<211> LENGTH: 107
<212> TYPE: PRT
<213> ORGANISM: Artificial sequence
<220> FEATURE:
<223> OTHER INFORMATION: Synthetic amino acid

<400> SEQUENCE: 14

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
                100                 105

<210> SEQ ID NO 15
<211> LENGTH: 450
<212> TYPE: PRT
<213> ORGANISM: Artificial sequence
<220> FEATURE:
<223> OTHER INFORMATION: Synthetic amino acid

<400> SEQUENCE: 15
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415
```

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 16
<211> LENGTH: 107
<212> TYPE: PRT
<213> ORGANISM: Artificial sequence
<220> FEATURE:
<223> OTHER INFORMATION: Synthetic amino acid

<400> SEQUENCE: 16

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 17
<211> LENGTH: 15
<212> TYPE: PRT
<213> ORGANISM: Artificial sequence
<220> FEATURE:
<223> OTHER INFORMATION: Synthetic amino acid

<400> SEQUENCE: 17

Gly Gly Gly Gly Ser Gly Gly Gly Gly Ser Gly Gly Gly Gly Ser
1               5                   10                  15

<210> SEQ ID NO 18
<211> LENGTH: 6
<212> TYPE: PRT
<213> ORGANISM: Artificial sequence
<220> FEATURE:
<223> OTHER INFORMATION: Synthetic amino acid

<400> SEQUENCE: 18

Ala Ser Thr Lys Gly Pro
1               5